(12) United States Patent
Sauvé et al.

(10) Patent No.: US 6,313,177 B1
(45) Date of Patent: Nov. 6, 2001

(54) D-MANNITOL DERIVATIVES AS HIV ASPARTYL PROTEASE INHIBITORS

(75) Inventors: Gilles Sauvé; Abderrahim Bouzide, both of Laval (CA)

(73) Assignee: Pharmacor Inc., Laval (CA)

( * ) Notice: Subject to any disclaimer, the term of this patent is extended or adjusted under 35 U.S.C. 154(b) by 0 days.

(21) Appl. No.: 09/302,185

(22) Filed: Apr. 30, 1999

(51) Int. Cl.[7] .............................. C07C 31/18; A61K 31/13

(52) U.S. Cl. ........................................ 514/669; 568/852

(58) Field of Search ............................. 568/852; 514/669

(56) References Cited

U.S. PATENT DOCUMENTS

| 4,804,789 | * | 2/1989 | Eibl ........................................ 568/853 |
| 5,811,512 |   | 9/1998 | Hirschmann et al. ............... 530/311 |

FOREIGN PATENT DOCUMENTS

| 0 098 600 A | 1/1984 | (EP) . |
| A-3239858 | 1/1984 | (DK) . |
| WOA9200948 | 1/1992 | (WO) . |
| WO-A-9216501 | 10/1992 | (WO) . |
| WO 94/13629 | 6/1994 | (WO) . |
| WO 94 17096 A | 8/1994 | (WO) . |
| WO 98 18473 A | 5/1998 | (WO) . |
| WO 98 50347 A | 11/1998 | (WO) . |
| WO 00/59867 | 10/2000 | (WO) . |

OTHER PUBLICATIONS

Fahey et al., Clin. Exp. Immunol.. vol. 88, pp. 1–5, (1992).*
Stein et al., Clinical Infectious Diseases, vol. 17, pp. 749–771, (1993).*
Fox, Bio/Technology, vol. 12, Feb. 1994.*
Hori et al., "Regioselective De–O–benzylation with Lewis Acids", Journal of Organic Chemistry, 1989, vol. 54, pp. 1346–1353.*
J. Med. Chem. 40 (6) 885–897 (1997).
Lasky L.A, et al., Cell. vol. 50, p. 975–985 (1987).
Haseltine W. A. FASEB J. vol. 5 2349–2360 (1991).
Goff S. P. J. Acq. Imm.Defic.Sydr., vol. 3, p. 817–831 (1990).
Sakai, H et al, J. Virol, vol. 67, p. 1169–1174 (1993).
Bukrinsky et al., Proc. Acad, Sci. USA, vol. 89, p. 6580–6584 (1992).
T.W. Greene, Protecting Groups in Organic Synthesis, John Wiley and Sons (1991).
Bouzide A. et al, Tet. Letters vol. 38, p. 5945–5948 (1997).
Gallay et al., Cell. vol. 80, p.379–388 (1995).
Active nuclear import of human immunodeficiency virus type 1 preintegration complexes, Proc. Natl. Acad. Sci. USA, vol. 89, p. 6580 to 6584 (Jul. 1992).

Inhibition of HIV–1 protease in infected T–lymphocytes by synthetic peptide analogues, Letters to Nature, vol. 343, p. 90 to 92, Jan. 4, 1990.
Integration is Essentual for Efficient Gene Expression of Human Immunodeficiency Virus Type 1, Journal of Virology, Mar. 1993, p. 1169 to 1174.
Delineation of a Region of the Human Immunodeficiency Virus Type 1 gp120 glycoprotein critical for interaction with the CD4 receptor, Cell. vol. 50, 975–985, Sep. 11, 1987, p. 975 to 985.
Molecular biology of the human immunodeficiency virus type 1, The Faseb Journal, p. 2349 to 2360, vol. 5, Jul. 1991.
Retroviral reverse transcriptase: Synthesis, Structure and Function, Journal of Acquired Immune Deficiency Syndromes, vol. 3, No. 8, 1990, p. 817 to 831.
Journal of the American Chemical Society, vol. 118, No. 33, p. 7647 to 7652, Aug. 21, 1996.
Chemical Abstracts, vol. 101, No. 1, H. Eibl "D–mannitol derivatives as raw products for the synthesis of phospholipids" Abstract No. 6942j(1984).
Chemical Abstracts, vol. 82, No. 5, A. I. Gurevich: "Synthesis sof (2S, 5S)–2, 5–dimethoxyadipic acid" . . . XP002146942 (1975).
Chemical Abstracts, vol. 77, No. 1, C.E. Ballou "L–glycero–tetrulose (L–erythrulose) 1–posphate", Abstract No. 5720j (1972).
Chemical Abstract, vol. 103, No. 7, L.V. Bakinovskii et al "1, 2–0–Cyanoalkylidene derivatives of furanose as 1, 2–trans–glycosylating agents" Abstract No. 54378t (1985).
Journal of the Chemical Society, Perkin Transactions 1 (1979).
Journal of Medicinal Chemistry, vol. 34, No. 8, p. 2305–2314, Aug. 1991.

(List continued on next page.)

Primary Examiner—Gary Geist
Assistant Examiner—Everett White
(74) Attorney, Agent, or Firm—Ronald S. Kosie; Robert Brouillette

(57) ABSTRACT

A D-mannitol derivative selected from the group consisting of a compound of formula

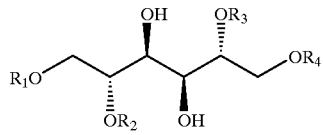

pharmaceutically acceptable derivatives thereof and where applicable or appropriate pharmaceutically acceptable salts thereof, wherein $R_1$, $R_2$, $R_3$ and $R_4$ are the same or different and may each independently be selected from among alkyl and aryl (i.e. aromatic including aromatic like) groups. The D-mannitol derivatives may be used as HIV aspartyl protease inhibitors.

22 Claims, No Drawings

OTHER PUBLICATIONS

HE Zhao et al. "Coumarin based inhibitors of HIV integrase", Journal of Medical Chemistry, US, American Chemical Society, Washington, vol. 40, No. 2, 1997.

Chemical Abstract, vol. 119, No. 21, A.N. Pinchuck: "Synthesis of enantiomerically pure ether lipid analogs from D–mannitol" . . . XP2146941, 1993.

A. Bouzide: "Lewis acid–catalyzed deprotection of p–metoxybenzyl ether" ... XP002146936, Oct. 1997.

K. Fukase: "Synthetic study of lipoteichoic acid of gram positive bacteria. I. Synthesis of proposed fundamental structure of Streptococcus pyogenes lipoteichoic acid" . . . XP002146937, 1992.

M. Fedeoronko: "Kinetics and mechanism of the acid–catalyzed reactions of methylated trioses" . . . XP002146938, 1980.

J.W. Van Cleve: "Syntheses of 3(4)–0–allyl–, 3(4)–0–benzyl– and 1, 2, 3(4), 5, 6–penta–0–benzoyl–D–mannitol" . . . XP002146939, 1982.

G. Zuccarello: "HIV–1 Protease inhibitors based on acyclic carbohydrates" . . . XP002146940, 1998.

U. Peters: "Platelet activating factor synthetic studies" . . . XP002146935, 1987.

\* cited by examiner

D-MANNITOL DERIVATIVES AS HIV ASPARTYL PROTEASE INHIBITORS

TECHNICAL FIELD OF THE INVENTION

The present invention relates to a compounds with aspartyl protease inhibitory properties. This invention in particular relates to D-mannitol derivatives with HIV aspartyl protease inhibitory properties that have been characterized by specific structural and physicochemical features. In addition, this invention also relates to pharmaceutical compositions exploiting these compounds. The compounds including the pharmaceutical compositions of this invention are able to inhibit the activity of HIV aspartyl protease. Accordingly, this inhibitory property may be advantageously used to provide compounds with antiviral properties against HIV viruses, including the HIV-1 and HIV-2 viruses.

BACKGROUND OF THE INVENTION

The HIV (human immunodeficiency virus) retrovirus is the causative agent for AIDS (acquired immunodeficiency syndrome). Thus the HIV-1 retrovirus primarily uses the CD4 receptor (a 58 kDa transmembrane protein) to gain entry into cells, through high-affinity interactions between the viral envelope glycoprotein (gp 120) and a specific region of the CD4 molecule found in T-lymphocytes and CD4 (+) T-helper cells (Lasky L. A. et al., Cell vol. 50, p. 975–985 (1987)). HIV infection is characterized by a period immediately following infection called "asymptomatic" which is devoid of clinical manifestations in the patient. Progressive HIV-induced destruction of the immune system then leads to increased susceptibility to opportunistic infections, which eventually produces a syndrom called AIDS-related complex (ARC) characterized by symptoms such as persistent generalized lymphadenopathy, fever, weight loss, followed itself by full blown AIDS.

After entry of the retrovirus into a cell, viral RNA is converted into DNA, which is then integrated into the host cell DNA. The reverse transcriptase encoded by the virus genome catalyzes the first of these reactions (Haseltine W. A. FASEB J. Vol. 5 2349–2360 (1991)). At least three functions have been attributed to the reverse transcriptase: RNA-dependent DNA polymerase activity which catalyzes the synthesis of the minus strand DNA from viral RNA, ribonuclease H (RNase H) activity which cleaves the RNA template from RNA-DNA hybrids and DNA-dependent DNA polymerase activity which catalyzes the synthesis of a second DNA strand from the minus strand DNA template (Goff S. P. J. Acq. Imm. Defic. Syndr., vol. 3 p. 817–831 (1990)). The double stranded DNA produced by reverse transcriptase, now called provirus, is then able to be inserted into host genomic DNA.

At the end of reverse transcription, the viral genome now in the form of DNA is integrated into host genomic DNA and serve as a template for viral gene expression by the host transcription system, which leads eventually to virus replication (Sakai, H al., J. Virol. Vol. 67, p. 1169–1174 (1993)). The preintegration complex consists of integrase, reverse transcriptase, p17 and proviral DNA (Bulrinsky et al., Proc. Nat. Acad. Sci. USA vol. 89, p. 6580–6584 (1992)). The phosphorylated p17 protein plays a key role in targeting the preintegration complex into the nucleus of host cell (Gallay et al., Cell, vol. 80, p. 379–388 (1995)).

The primary RNA transcripts made from the provirus are synthesized by the host cell RNA polymerase II which is modulated by two virus-encoded proteins called Tat and Rev. The viral proteins are formed as polyproteins.

Post-translational modifications of viral polyproteins include processing and glycosylation of Env (envelope) proteins, and myristylation of the N-terminal residue of the p17 protein in the Gag and Gag-Pol polyproteins. The latter two precursors correspond to structural proteins and viral enzymes. The viral protease is involved in processing polyproteins Gag and. Gag-Pol into mature proteins, a step essential for virus infectivity.

A number of synthetic antiviral agents have been designed to block various stages in the replication cycle of HIV. These agents include compounds which interfere with viral binding to CD4 T-lymphocytes (for example, soluble CD4), compounds which block viral reverse transcriptase (for example, didanosine and zidovudine (AZT)), budding of virion from the cell (interferon), or the viral protease (for example Ritonavir and Indinavir). Some of these agents proved ineffective in clinical tests. Others, targeting primarily early stages of viral replication, have no effect on the production of infectious virions in chronically infected cells. Furthermore, administration of many of these agents in effective therapeutic doses has led to cell-toxicity and unwanted side effects, such as anemia, neurotoxicity and bone marrow suppression.

Anti-protease compounds represent the most recent drugs developed to block HIV replication. These compounds inhibit the formation of infectious virions by interfering with the processing of viral polyprotein precursors. Thus, the antiviral potential of HIV protease inhibition has been demonstrated using peptidic inhibitors. Such peptidic compounds, however, are typically large and complex molecules that tend to exhibit poor bioavailability and are not generally consistent with oral administration. Accordingly, the need exists for compounds that can effectively inhibit the action of viral proteases, for use as agents for preventing and treating chronic and acute viral infections, such as HIV.

SUMMARY OF THE INVENTION

The present invention relates to mannitol derivatives, including their pharmaceutically acceptable derivatives. These compounds have an affinity for aspartyl proteases, in particular, HIV aspartyl protease. Therefore, these compounds may be useful as inhibitors of such proteases. These compounds may be used alone or in combination with other therapeutic or prophylactic agents, such as antivirals, antibiotics, immunomodulators or vaccines, for the treatment or prophylaxis of viral infection.

Compounds of this invention are capable of inhibiting HIV viral replication in human CD4+ T-cells, by inhibiting the ability of HIV aspartyl proteases to catalyze the hydrolysis of peptide bonds. These novel compounds can thus serve to reduce the production of infectious virions from acutely and chronically infected cells, and can inhibit the initial or further infection of host cells. Accordingly, these compounds may be useful as therapeutic and prophylactic agents to treat or prevent infection by HIV-1 and related viruses, which may result in asymptomatic HIV-1 infection, AIDS-related complex (ARC), acquired immunodeficiency syndrome (AIDS), AIDS-related dementia, or similar diseases of the immune system.

Acccordingly, the present invention relates to D-mannitol derivatives that may be used as aspartyl protease inhibitors, and particularly, HIV aspartyl protease inhibitors.

Accordingly, the present invention provides a D-mannitol derivative selected from the group consisting of a compound of formula 1

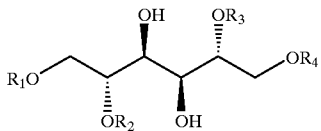

pharmaceutically acceptable derivatives thereof and where applicable or appropriate pharmaceutically acceptable salts thereof, wherein $R_1$, $R_2$, $R_3$ and $R_4$ are the same or different and may each independently be selected from among alkyl and aryl (i.e. aromatic including aromatic like) groups. The aromatic (or aromatic like) group may be an aromatic hydrocarbon group, an aromatic heterocyclic group, an allyl group, a cyclopropylmethyl group, a alkylthiothioxo group, an aroyl group and the like.

In addition, this invention provides pharmaceutical compositions in which the D-mannitol derivatives (e.g. derived from D-mannitol) may be used to inhibit aspartyl proteases, including HIV aspartyl proteases, thus providing protection against HIV infection.

The term "heterocycle" "heterocyclic group" and the like refer to a stable 5–7 membered monocycle or bicyclic heterocycle, which may be optionally benzofused or heterocyclofused. Each heterocycle consists of carbon atoms and from one to four heteroatoms selected from the group consisting of nitrogen, oxygen and sulfiir. As used herein, the terms "nitrogen and sulfur heteroatoms" include any oxidized form of nitrogen and sulfur, and the quaternized form of any basic nitrogen. The heterocyclic ring may be attached by any heteroatom or carbon atom of the cycle, which may for example give rise to benzimidazolyl, imidazolyl, imidazolinyl, imidazolidinyl, quinolyl, isoquinolyl, indolyl, pyridyl, pyrrolyl, pyrrolinyl, pyrrolidinyl, pyrazolyl, pyrazinyl, quinoxolyl, piperidinyl, morpholinyl, β-carbolinyl, tetrazolyl, thiazolidinyl, benzofuranyl, thiamorpholinyl, benzoxazolyl, oxopiperidinyl, oxopyrrolidinyl, oxoazepinyl, azepinyl, isoxazolyl, tetrahydropyranyl, tetrahydrofuranyl, thiadiazolyl, thiadiazinyl, benzodioxolyl, thiophenyl, tetrahydrothiophenyl, nicoticoyl, morpholinecarbodithioyl and sulfolanyl.

The substituents $R_1$, $R_2$, $R_3$ and $R_4$ for the compound of formula 1 above may, for example, be selected from the group consisting of $C_1$ to $C_5$ alkyl (e.g. methyl),
—($C_1$ to $C_5$ alkylene)$_m$—Ar
—(C=O)—($C_1$ to $C_5$ alkylene)$_m$—Ar
—(C=S)—($C_1$ to $C_5$ alkylene)$_m$—Ar
—(C=O)—O—$CH_2$—Ar
—(C=S)—S—$CH_2$—Ar
and —(C=S)—S—$CH_3$ wherein m denotes 0 or 1 and Ar is an unsubstituted aromatic (or aromatic like) group or a mono or polysubstituted aromatic (or aromatic like) group. The group Ar may for example be an unsubstituted or substituted benzyl group (i.e. m=1, alkylene=methylene and Ar=unsubstituted or substituted phenyl). The aromatic (or aromatic like) group may, for example, be substituted by one or more members of the group consisting of halogen atoms, amino groups, amino acid groups, carboxylic acid groups, alkylthio groups, cyano groups, hydroxyl, alkoxy groups, carbonyl groups, etc. The aromatic (or aromatic like) group may, for example, be 2-thienylmethyl, 2-,3-,4-pyridylmethyl, 2-naphthylmethyl, allyl, cyclopropylmethyl, and the like.

More particularly the group Ar may be selected from the group consisting of allyl, vinyl, styryl, cyclopropyl, naphthyl, aromatic heterocyclic groups (such as pyridyl and thienyl), unsubstituted phenyl and phenyl which is substituted by one or more members of the group consisting of —Cl, —F, —Br, —I, —CN, —A—CN, —$CF_3$, —A—$CF_3$, —$NO_2$, $R_5$—CO, $R_5$—CO—A—, —$OCH_2C_6H_5$, —A—S$(O)_n$—$R_5$, straight or branched $C_1$ to $C_6$ alkyl, —A—$OR_5$, —$OR_5$, —$NR_6R_7$, —A—$NR_6R_7$, —$COOR_8$, —A—$COOR_8$, —A—$NHCOR_8$, —$NHCOOR_8$ and —A—$NHCOOR_8$, wherein n denotes 0, 1 or 2, A represents an alkylene group having from 1 to 5 carbon atoms (e.g. methylene), $R_5$ is selected from the group consisting of H and straight or branched $C_1$ to $C_6$ alkyl, straight or branched $C_2$ to $C_6$ alkenyl, $C_4$ to $C_{11}$ methylcycloalkyl, phenyl, mono- or poly-substituted phenyl, benzimidazolyl, imidazolyl, imidazolinyl, imidazolidinyl, quinolyl, isoquinolyl, indolyl, pyridyl, pyrrolyl, pyrrolinyl, pyrrolidinyl, pyrazolyl, pyrazinyl, quinoxolyl, piperidinyl, morpholinyl, β-β-carbolinyl, tetrazolyl, thiazolidinyl, benzofuranyl, thiamorpholinyl, benzoxazolyl, oxopiperidinyl, oxopyrrolidinyl, oxoazepinyl, azepinyl, isoxazolyl, tetrahydropyranyl, tetrahydrofuranyl, thiadiazolyl, thiadiazinyl, benzodioxolyl, thiophenyl, tetrahydrothiophenyl, nicoticoyl, morpholinecarbodithioyl and sulfolanyl;

$R_6$ and $R_7$ are each and independently selected from the group consisting of H and straight or branched $C_1$ to $C_6$ alkyl, straight or branched $C_2$ to $C_6$ alkenyl, $C_4$ to $C_{11}$ methylcycloalkyl, phenyl, mono- or poly-substituted phenyl, benzimidazolyl, imidazolyl, imidazolinyl, imidazolidinyl, quinolyl, isoquinolyl, indolyl, pyridyl, pyrrolyl, pyrrolinyl, pyrrolidinyl, pyrazolyl, pyrazinyl, quinoxolyl, piperidinyl, morpholinyl, β-carbolinyl, tetrazolyl, thiazolidinyl, benzofuranyl, thiamorpholinyl, benzoxazolyl, oxopiperidinyl, oxopyrrolidinyl, oxoazepinyl, azepinyl, isoxazolyl, tetrahydropyranyl, tetrahydrofuranyl, thiadiazolyl, thiadiazinyl, benzodioxolyl, thiophenyl, tetrahydrothiophenyl, nicoticoyl, morpholinecarbodithioyl and sulfolanyl or $R_6$ and $R_7$ together with the nitrogen atom to which they are bonded represent a (saturated or unsaturated) heterocyclic group of formula

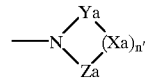

wherein Ya and Za each independently denotes a hydrocarbon chain comprising 1 to 3 carbon atoms, Xa denotes O and n' denotes 0 or 1, provided that when n' denotes 1 Ya and Za cannot both comprise 3 carbon atoms at the same timeand that when n' denotes 0 Ya and Za are bonded directly together (e.g. the heterocyclic may be pyridyl, morpholinyl and the like) and;

$R_8$ is selected from the group consisting of H and straight or branched $C_1$ to $C_6$ alkyl, straight or branched $C_2$ to $C_6$ alkenyl, $C_4$ to $C_{11}$ methylcycloalkyl, phenyl, mono- or poly-substituted phenyl, benzimidazolyl, imidazolyl, imidazolinyl, imidazolidinyl, quinolyl, isoquinolyl, indolyl, pyridyl, pyrrolyl, pyrrolinyl, pyrrolidinyl, pyrazolyl, pyrazinyl, quinoxolyl, piperidinyl, morpholinyl, β-carbolinyl, tetrazolyl, thiazolidinyl, benzofuranyl, thiamorpholinyl, benzoxazolyl, oxopiperidinyl, oxopyrrolidinyl, oxoazepinyl, azepinyl, isoxazolyl, tetrahydropyranyl, tetrahydrofuranyl, thiadiazolyl, thiadiazinyl, benzodioxolyl, thiophenyl, tetrahydrothiophenyl, nicoticoyl, morpholinecarbodithioyl and sulfolanyl.

The present invention, in particular, provides a compound of formula 1:

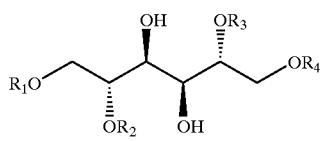

1 pharmaceutically acceptable derivatives thereof and where applicable or appropriate pharmaceutically acceptable salts thereof, wherein $R_1$, $R_2$, $R_3$ and $R_4$ are each independently (i.e. same or different) selected from the group consisting of unsubstituted benzyl and benzyl which is substituted by one or more members of the group consisting of —Cl, —F, —Br, —I, —CN, —A—CN, —CF$_3$, —A—CF$_3$, —NO$_2$, $R_5$—CO, $R_5$—CO—A—, —OCH$_2$C$_6$H$_5$, —A—S(O)$_n$—R$_5$, straight or branched C$_1$ to C$_6$ alkyl, —A—OR$_5$, —OR$_5$, —NR$_6$R$_7$, —A—NR$_6$R$_7$, —COOR$_8$, —A—COOR$_8$, —A—NHCOR$_8$, —NHCOOR$_8$ and —A—NHCOOR$_8$, wherein n denotes 0, 1 or 2, A represents an alkylene group having from 1 to 5 carbon atoms, $R_5$ is selected from the group consisting of H and straight or branched C$_1$ to C$_6$ alkyl, straight or branched C$_2$ to C$_6$ alkenyl, C$_4$ to C$_{11}$ methylcycloalkyl, phenyl, mono- or poly-substituted phenyl, benzimidazolyl, imidazolyl, imidazolinyl, imidazolidinyl, quinolyl, isoquinolyl, indolyl, pyridyl, pyrrolyl, pyrrolinyl, pyrrolidinyl, pyrazolyl, pyrazinyl, quinoxolyl, piperidinyl, morpholinyl, β-carbolinyl, tetrazolyl, thiazolidinyl, benzofuranyl, thiamorpholinyl, benzoxazolyl, oxopiperidinyl, oxopyrrolidinyl, oxoazepinyl, azepinyl, isoxazolyl, tetrahydropyranyl, tetrahydrofuranyl, thiadiazolyl, thiadiazinyl, benzodioxolyl, thiophenyl, tetrahydrothiophenyl, nicoticoyl, morpholinecarbodithioyl and sulfolanyl;

$R_6$ and $R_7$ are each and independently selected from the group consisting of H and straight or branched C$_1$ to C$_6$ alkyl, straight or branched C$_2$ to C$_6$ alkenyl, C$_4$ to C$_{11}$ methylcycloalkyl, phenyl, mono- or poly-substituted phenyl, benzimidazolyl, imidazolyl, imidazolinyl, imidazolidinyl, quinolyl, isoquinolyl, indolyl, pyridyl, pyrrolyl, pyrrolinyl, pyrrolidinyl, pyrazolyl, pyrazinyl, quinoxolyl, piperidinyl, morpholinyl, β-carbolinyl, tetrazolyl, thiazolidinyl, benzofuranyl, thiamorpholinyl, benzoxazolyl, oxopiperidinyl, oxopyrrolidinyl, oxoazepinyl, azepinyl, isoxazolyl, tetrahydropyranyl, tetrahydrofuranyl, thiadiazolyl, thiadiazinyl, benzodioxolyl, thiophenyl, tetrahydrothiophenyl, nicoticoyl, morpholinecarbodithioyl and sulfolanyl or $R_6$ and $R_7$ together with the nitrogen atom to which they are bonded represent a (saturated or unsaturated) heterocyclic group of formula

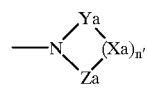

wherein Ya and Za each independently denotes a normal (i.e. unbranched) hydrocarbon chain comprising 1 to 3 carbon atoms, Xa denotes O and n' denotes 0 or 1, provided that when n' denotes 1 Ya and Za cannot both comprise 3 carbon atoms at the same time and that when n' denotes 0 Ya and Za are bonded directly together (e.g. the heterocyclic may be pyridyl, morpholinyl and the like), and;

$R_6$ is selected from the group consisting of H and straight or branched C$_1$ to C$_6$ alkyl, straight or branched C$_2$ to C$_6$ alkenyl, C$_4$ to C$_{11}$ methylcycloalkyl, phenyl, mono- or poly-substituted phenyl, benzimidazolyl, imidazolyl, imidazolinyl, imidazolidinyl, quinolyl, isoquinolyl, indolyl, pyridyl, pyrrolyl, pyrrolinyl, pyrrolidinyl, pyrazolyl, pyrazinyl, quinoxolyl, piperidinyl, morpholinyl, β-carbolinyl, tetrazolyl, thiazolidinyl, benzofuranyl, thiamorpholinyl, benzoxazolyl, oxopiperidinyl, oxopyrrolidinyl, oxoazepinyl, azepinyl, isoxazolyl, tetrahydropyranyl, tetrahydrofuranyl, thiadiazolyl, thiadiazinyl, benzodioxolyl, thiophenyl, tetrahydrothiophenyl, nicoticoyl, morpholinecarbodithioyl and sulfolanyl.

Combinations of substituents and variables envisioned by this invention are only those that result in the formation of stable compounds. The term "stable", as used herein, refers to compounds which possess stability sufficient to allow manufacture and administration to a mammal by methods known in the art. Typically, such compounds are stable at a temperature of 40° C. or less, in the absence of moisture or other chemically reactive conditions, for at least a week.

The compounds of formulal this invention contain one or more asymmetric carbon atoms and thus may occur as racemates and racemic mixtures, single enantiomer, diastereomeric mixtures and individual diastereoisomers. All such isomeric forms of these compounds are expressly included in the present invention. Each stereogenic carbon may be of the R or S configuration.

The terms "HIV protease" and "HIV aspartyl protease" are used interchangeably and refer to the aspartyl protease encoded by the human immunodeficiency virus type 1 or 2. In a preferred embodiment of this invention, these terms refer to the human immunodeficiency virus type 1 aspartyl protease.

The term "pharmaceutically effective amount" refers to an amount effective in treating IV infection in a patient.

The term "prophylactically effective amount" refers to an amount effective in preventing HIV infection in a patient. As used herein, the term "patient" refers to a mammal, including a human.

The term "pharmaceutically acceptable carrier or adjuvant" and "physiologically acceptable vehicle" refer to a non-toxic carrier or adjuvant that may be administered to a patient, together with a compound of this invention, and which does not destroy the pharmacological activity thereof.

As used herein, the compounds of formulal of this invention, are to be to be understood as being defined to include pharmaceutically acceptable derivatives thereof. Thus a "pharmaceutically acceptable derivative" means any pharmaceutically acceptable salt, ester, or salt of such ester, of a compound of formulal of this invention as well as any other compound which, upon administration to a recipient, is capable of providing (directly or indirectly) a compound of this invention or an antivirally active metabolite or residue thereof.

Salts derived from appropriate bases include alkali metal (e.g., sodium), alkaline earth metal (e.g., magnesium), ammonium and N—$(C_{1-4}alkyl)_4^+$ salts.

Pharmaceutically acceptable salts of the compounds of this invention include those derived from pharmaceutically acceptable inorganic and organic acids and bases. Examples of such acid salts include: acetate, adipate, alginate, aspartate, benzoate, benzenesulfonate, bisulfate, butyrate, citrate, camphorate, camphorsulfonate, cyclopentanepropionate, digluconate, dodecylhydrogensulfate. dodecylsulfate, ethanesulfonate, formate, fumarate, glucoheptanoate, glycerophosphate, glycollate, hemisulfate, heptanoate, hexanoate, hydrochloride, hydrobromide, hydroiodide, 2-hydroxyethanesulfonate, lactate, maleate, malonate, methanesulfonate, 2-naphthylsulfonate, nicotinate, nitrate, oxalate, pamoate, pectinate, perchlorate, persulfate, 3-phenylpropionate, phosphate, picrate, pivalate, propionate, salicylate, succinate, sulfate, tartrate, thiocyanate, tosylate, and undecanoate.

This invention also envisions the quatemization of any basic nitrogen containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides, and aralkyl halides including benzyl and phenethyl bromides. Water or oil-soluble or dispersible products may be obtained by such quaternization.

The compounds of this invention are readily prepared using conventional techniques from commercially available and cheap starting materials.

The compounds of this invention are among the most readily prepared HIV protease inhibitors known at this point. Previously described HIV protease inhibitors are resulting from long synthetic sequences and contain more than six chiral centers, numerous peptide bonds and require air-sensitive reagents such as organometallic complexes to achieve their successful preparations. The relative ease of synthesis of the products described in this invention represent a marked advantage, especially for the large scale preparation of these compounds.

In general, D-mannitol derivatives of formulal are readily obtained from commercially available D-mannitol or derivatives of D-mannitol through known synthetic sequences. Using standard techniques, D- or L-mannitol may be transformed to the desired HIV protease inhibitors according to Scheme 1, as described below; Scheme 1 illustrates the preparation of 1,2,5,6-tetrasubstituted O-benzyl D-mannitol derivatives.

SCHEME 1

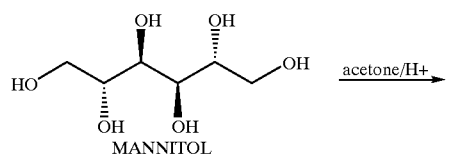
MANNITOL

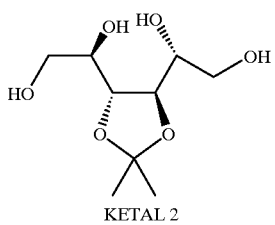
KETAL 2

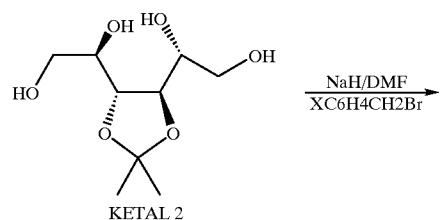
KETAL 2

NaH/DMF
XC6H4CH2Br

X = substituent

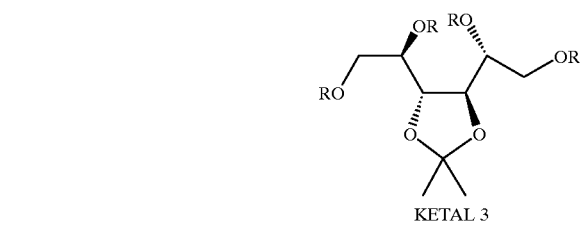
KETAL 3

KETAL 3

MeOH/HCl

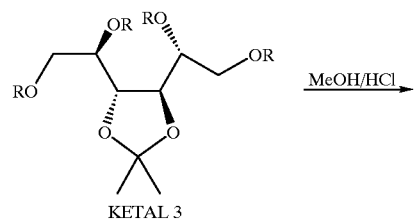
BENZYL MANNITOL 4

R = XC6H4CH2—

Thus D-mannitol is converted to its 3,4-monoketal using acetone or other ketones krnown to those skilled in the art. (T. W. Greene, Protecting Groups in Organic Synthesis, John Wiley and Sons (1991) and references cited therein). The ketal 2 is then easily aukylated on the four free hydroxyl groups using sodium hydride in DMF and a substituted benzyl halide providing the tetrabenzylated ketal 3 in excellent yield. The ketal group is then readily hydrolysed using methanol (MeOH) containing hydrochloric acid providing the desired tetrasubstituted benzyl D mannitol derivatives 4 in excellent yields.

Scheme 2, below, illustrates the preparation of 1,6-similarly disubstituted and 2,5-similarly disubstituted O-benzyl derivatives.

SCHEME 2

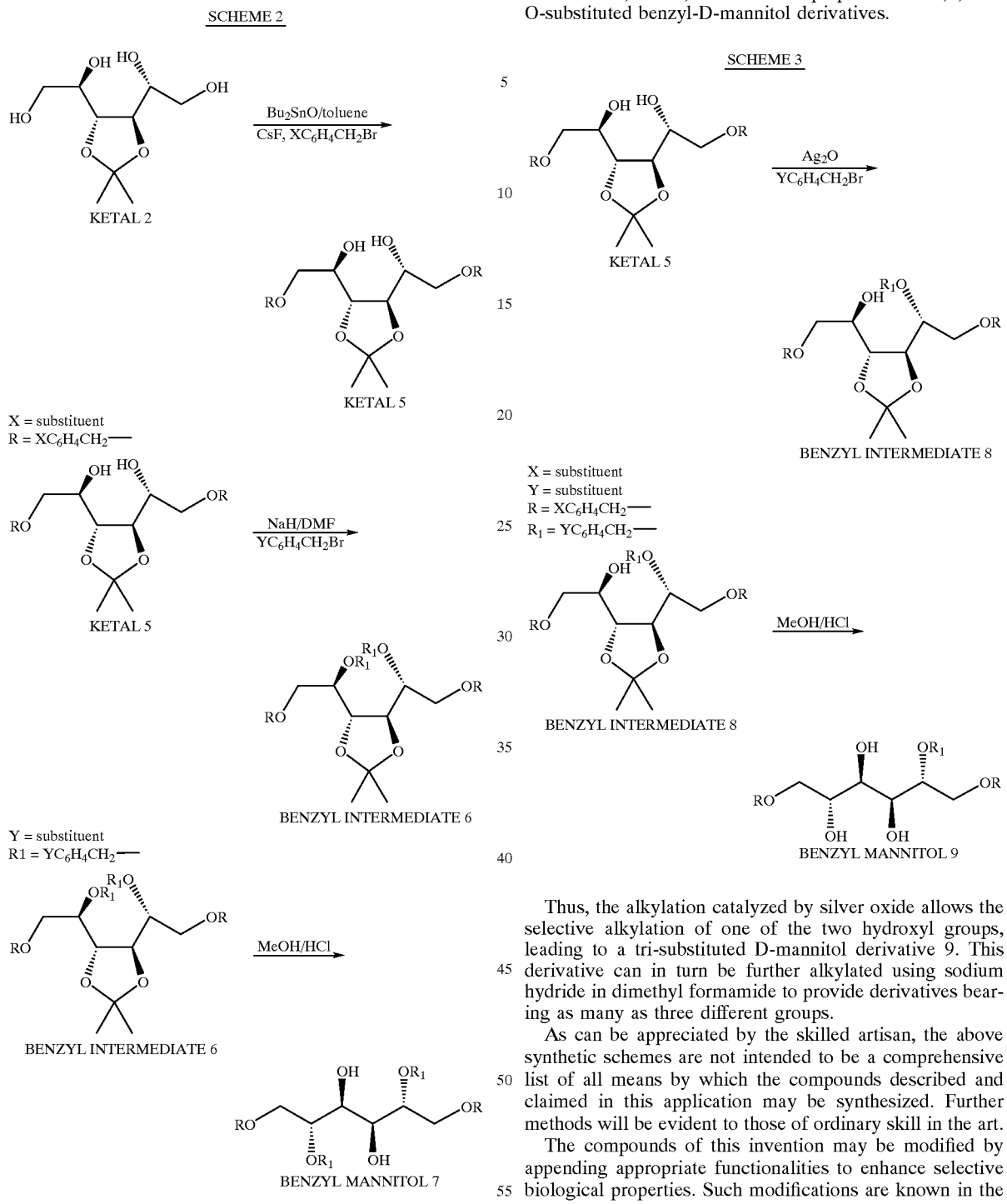

Scheme 3, below, illustrates the preparation of 1,2,5-tri-O-substituted benzyl-D-mannitol derivatives.

SCHEME 3

As shown in Scheme 2, the ketal 2 can be alkylated selectively using butyl tin oxide in toluene following the indications of Bouzide A. et al, Tet. Letters vol. 38, p. 5945–5948 (1997), cesium fluoride and the alkylating agent such as a substituted benzyl halide to yield the 1,6-dibenzylated intermediate 5 that can subsequently be alkylated using the sodium hydride in DMF method with a different alkylating substituted benzyl halide to provide derivatives such as 7, bearing a similar benzyl groups at position 1 and 6 of the D-mannitol and two different substituted benzyl groups at position 2 and 5.

Thus, the alkylation catalyzed by silver oxide allows the selective alkylation of one of the two hydroxyl groups, leading to a tri-substituted D-mannitol derivative 9. This derivative can in turn be further alkylated using sodium hydride in dimethyl formamide to provide derivatives bearing as many as three different groups.

As can be appreciated by the skilled artisan, the above synthetic schemes are not intended to be a comprehensive list of all means by which the compounds described and claimed in this application may be synthesized. Further methods will be evident to those of ordinary skill in the art.

The compounds of this invention may be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injhection, alter metabolism and alter rate of excretion.

As discussed above, the novel compounds of the present invention are excellent ligands for aspartyl proteases, particularly HIV-1 protease. Accordingly, these compounds are capable of targeting and inhibiting late stage events in the replication, i.e.; the processing of the viral polyproteins by HIV encoded protease. Compounds according to this invention advantageously inhibit the ability of the HIV-1 virus to infect immortalized human T cells over a period of days, as determined by an assay of extracellular p24 antigen—a specific marker of viral replication (see, Meek et al., Nature, 343, pp. 90–92 (1990)).

In addition to their use in the prophylaxis or treatment of HIV or HTLV infection, the compounds according to this invention may also be used as inhibitory or interruptive agents for other viruses which depend on aspartyl proteases, similar to HIV or HTLV aspartyl proteases, for obligatory events in their life cycle. Such compounds inhibit the proteolytic processing of viral polyprotein precursors by inhibiting aspartyl protease. Because aspartyl protease is essential for the production of mature virions, inhibition of that processing effectively blocks the spread of virus by inhibiting the production and reproduction of infectious virions, particularly from chronically infected cells. The compounds of this invention advantageously inhibit aspartyl proteases, thus blocking the ability of aspartyl proteases to catalyze the hydrolysis of peptide bonds.

The compounds of this invention may be employed in a conventional manner for the treatment or prevention of HIV, HTLV, and other viruses, which depend on aspartyl proteases for obligatory events in their life cycle. Such methods of treatment, their dosage levels and requirements may be selected by those of ordinary skill in the art from available methods and techniques. For example, a compound of this invention may be combined with a pharmaceutically acceptable adjuvant for administration to a virally infected patient in a pharmaceutically acceptable manner and in an amount effective to lessen the severity of the viral infection.

Alternatively, the compounds of this invention may be used in vaccines and methods for protecting individuals against viral infection over an extended period of time. The compounds may be employed in such vaccines either alone or together with other compounds of this invention in a manner consistent with the conventional utilization of protease inhibitors in vaccines. For example, a compound of this invention may be combined with pharmaceutically acceptable adjuvants conventionally employed in vaccines and administered in prophylactically effective amounts to protect individuals over an extended period of time against viral infections, such as HIV infection. As such, the novel protease inhibitors of this invention can be administered as agents for treating or preventing viral infections, including HIV infection, in a mammal.

The compounds of this invention may be administered to a healthy or HIV-infected patient either as a single agent or in combination with other antiviral agents which interfere with the replication cycle of HIV. By administering the compounds of this invention with other antiviral agents which target different events in the viral life cycle, the therapeutic effect of these compounds is potentiated. For instance, the co-administered antiviral agent can be one which targets early events in the life viral cycle, such as cell entry, reverse transcription and viral DNA integration into cellular DNA. Antiviral agents targeting such early life cycle events include didanosine (ddI), zalcitabine (ddC), stavudine (d4T), zidovudine (AZT), polysulfated polysaccharides, sT4 (soluble CD4)—which blocks attachment or adsorption of the virus to host cells—and other compounds which block binding of virus to CD4 receptors on CD4 bearing T-lymphocytes. Other retroviral reverse transcriptase inhibitors, such as derivatives of AZT, may also be co-administered with the compounds of this invention to provide therapeutic treatment for substantially reducing or eliminating viral infectivity and the symptoms associated therewith. Examples of other antiviral agents include ganciclovir, dideoxycytidine, trisodium phosphonoformate, eflornithine, ribavirin, acyclovir, alpha interferon and trimenotrexate. Additionally, non-nucleoside inhibitors of reverse transcriptase, such as TIBO or nevirapine, may be used to potentiate the effect of the compounds of this invention, as may viral uncoating inhibitors, inhibitors of trans-activating proteins such as tat or rev, antisense molecules or inhibitors of the viral integrase. These compounds may also be co-administered with other inhibitors of HIV aspartyl protease.

Combination therapies according to this invention exert a synergistic effect in inhibiting HIV replication because each component agent of the combination acts on a different site of HIV replication. The use of such combinations also advantageously reduces the dosage of a given conventional anti-retroviral agent that would be required for a desired therapeutic or prophylactic effect as compared to when that agent is administered as a monotherapy. These combinations may reduce or eliminate the side effects of conventional single anti-retroviral agent therapies while not interfering with the anti-retroviral activity of those agents. These combinations reduce potential of resistance to single agent therapies, while minimizing any associated toxicity. These combinations may also increase the efficacy of the conventional agent without increasing the associated toxicity.

Preferred combination therapies include the administration of a compound of this invention with AZT, 3TC, ddI, ddC or d4T.

Alternatively, the compounds of this invention may also be co-administered with other HIV protease inhibitors such as Ro 31-8959 (Roche), L-735,524 (Merck), XM 323 (Dupont Merck) and A-80,987 (Abbott) to increase the effect of therapy or prophylaxis against various viral mutants or members of other HIV quasi species.

We prefer administering the compounds of this invention as single agents or in combination with retroviral reverse transcriptase inhibitors, such as derivatives of AZT or other HIV aspartyl protease inhibitors. We believe that the co-administration of the compounds of this invention with retroviral reverse transcriptase inhibitors or HIV aspartyl protease inhibitors may exert a substantial synergistic effect, thereby preventing, substantially reducing, or completely eliminating viral infectivity and its associated symptoms.

The compounds of this invention can also be administered in combination with immunomodulators (e.g., bropirimine, anti-human alpha interferon antibody, IL-2, GM-CSF, methionine enkephalin, interferon alpha, diethyldithiocarbamate, tumor necrosis factor, naltrexone and rEPO); antibiotics (e.g., pentamidine isethionate) or vaccines to prevent or combat infection and disease associated with HIV infection, such as AIDS and ARC.

When the compounds of this invention are administered in combination therapies with other agents, they may be administered sequentially or concurrently to the patient. Alternatively, pharmaceutical or prophylactic compositions according to this invention may be comprised of a combination of an aspartyl protease inhibitor of this invention and another therapeutic or prophylactic agent.

Although this invention focuses on the use of the compounds disclosed herein for preventing and treating HIV infection, the compounds of this invention can also be used as inhibitory agents for other viruses that depend on similar aspartyl proteases for obligatory events in their life cycle. These viruses include, but are not limited to other AIDS-like diseases caused by retroviruses, such as simian immunodeficiency viruses, HIV-2, HTLV-I and HTLV-II. In addition, the compounds of this invention may also be used to inhibit other aspartyl proteases and, in particular, other human aspartyl proteases including renin and aspartyl proteases that process endothelin precursors.

Pharmaceutical compositions of this invention comprise any of the compounds of the present invention, and pharmaceutically acceptable salts thereof, with any pharmacentically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albutin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethyleneglycol, sodium carboxymethylcellulose, polyacrylates, waxes, polyethylene-polyoxypropylene-block polymers, polyethylene glycol and wool fat.

The pharmaceutical compositions of this invention may be administered orally, parenterally by inhalation spray, topically, rectally, nasally, buccally, vaginally or via an implanted reservoir. We prefer oral administration or administration by injection. The pharmaceutical compositions of this invention may contain any conventional non-toxic pharmaceutically acceptable carriers, adjuvants or vehicles. The term "parenteral" as used herein includes subcutaneous, intracutaneous, intravenous, intramuscular, intra-articular, intrasynovial, intrastemal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceuticallly-acceptable oils, such as olive oil or castor oil, especially in their polyoxyethylated versions. These oil solutions or suspensions may also contain a long-chain alcohol diluent or dispersant, such as Ph. Helv. or a similar alcohol.

The pharmaceutical compositions of this invention may be orally administered in any orally acceptable dosage form including, but not limited to, capsules, tablets, and aqueous suspension and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax, and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical compositions can be formulated with a suitable lotion or cream containing the active compound suspended or dissolved in a carrier. Suitable carriers include, but are not limited to, mineral oil, sorbitan monostearate, polysorbate 60, cetyl esters wax cetearyl alcohol, 2-octyldodecanol, benzyl alcohol and water. The pharmaceutical compositions of this invention may also be topically applied to the lower intestinal tract by rectal suppository formulation or in a suitable neat formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline employing benzyl alcohol or other suitable preservatives, absorption promoters to enhance bioavailability, fluorocarbons, and/or other solubilizing or dispersing agents known in the art.

Dosage levels of between about 0.01 and about 25 mg/kg body weight per day, preferably between about 0.5 and about 25 mg/kg body weight per day of the active ingredient compound are useful in the prevention and treatment of viral infection, including HIV infection. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the patient treated and the particular mode of administration. A typical preparation may contain from about 5% to about 65% active compound (w/w). Preferably, such preparations may contain from about 20% to about 65% active compound.

Upon improvement of a patient's condition, a maintenance dose of a compound, composition or combination of this invention may be administered if necessary. Subsequently, the dosage or frequency of administration, or both, may be reduced, as a function of the symptoms, to a level at which the improved condition is retained. When the symptoms have been alleviated to the desired level, treatment should cease. Patients may, however, require intermittent treatment on a long-term basis, upon any recurrence of disease symptoms.

As the skilled artisan will appreciate, lower or higher doses than those recited above may be required. Specific dosage and treatment regimen for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

The compounds of this invention are also useful as commercial reagents which effectively bind to aspartyl proteases, particularly HIV aspartyl protease. As commercial reagents, the compounds of this invention, and their derivatives, may be used to block proteolysis of a target peptide, such as an aspartyl protease, or may be derivatized to bind to a stable resin as a tethered substrate for affinity chromatography applications. These and other uses which characterize commercial aspartyl protease inhibitors will be evident to those of ordinary skill in the art.

Enzymatic Assay for Determining the Inhibition Constant (Ki) of Synthetic Compounds Prepared Against the HIV Protease This is a fluorometric assay based on the cleavage by protease of a substrate carrying a donor group (EDANS, excitation at 340 nM and emission at 490 nM) and an acceptor group (DABCYL) on each side of the cleavage site, interacting together through fluorescence resonance energy transfer (FRET). Cleavage of the substrate by protease stops energy exchange between the two groups, resulting in a time-dependent increase in fluorescence intensity that is linearly related to the extent of substrate hydrolysis.

The enzymatic assay is done at 30° C. in a spectrophotometer microcuvet, in a total volume of 400 μL. The apparatus used for readings is a UV-visible Cary 1 spectrophotometer made by Varian. The reaction is run first in the absence of protease inhibitors for 2 min, using 355 μL of buffer at pH 4.7 (sodium acetate 100 mM, NaCl 1 M, EDTA 1 mM, DTT 1 mM, dimethylsulfoxide 10%, and BSA 1 mg/mL), 40 μL of substrate H-2930 from Molecular Probes (final concentration 10 μM) and 5 μL of recombinant HIV-1 protease (final concentration 18.3 nM) purchased from Bachem Bioscience. Fluorescence readings at 490 nM are taken continuously during the reaction, allowing determination of the enzyme's initial velocity ($v_o$). At the end of the 2 min incubation, the potential inhibitor at a defined concentration in a volume of 2 μL is added to the reaction, and fluorescence readings are taken for another 2 min, allowing determination of enzyme velocity ($v_i$) in the presence of the inhibitory compound. Several concentrations of the putative inhibitors are tested in the assay. After calculation of $v_o$ and $v_i$, the inhibition constant (Ki) of the compound is determined using the equation of Henderson:

$$\frac{Vo}{Vi} = 1 + \frac{[I]}{Ki_{app}} \text{ where } Ki = \frac{Ki_{app}}{1 + \frac{[S]}{Km}}$$

and [I]=inhibitor concentration, [S]=substrate concentration, Km=Michaelis-Menten constant, $Ki_{app}$=apparent Ki Note that the Michaelis-Menten constant of HIV protease is determined by running the assay without inhibitors, using several concentrations of substrate, and plotting the results as a Cornish-Bowden graph with the ratio substrate concentration/velocity as the ordinate and substrate concentration as the abscissa.

The compounds listed in Table 1 were prepared by following Schemes 1, 2 or 3 above. The activities of the compounds are also listed in the same table demonstrating their potential usefulness. In Table 1 are shown compounds of formula 1, as defined above, wherein $R_1$, $R_2$, $R_3$, $R_4$, the same or different, denote a benzyl group of formula

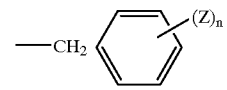

wherein Z is a substituent as shown in table 1 and wherein n, which may be 0, 1, 2, 3, 4 or 5 indicates the number of substituents on the phenyl ring, e.g. in the table if Z is fluorine and the phenyl ring has two fluorine atoms (i.e. n=2) this is shown in table 1 as 2,4-$F_2$ (the numbers 2 and 4 indicating the position of the fluorine substituents on the phenyl ring). Unless indicated otherwise in Table 1, n is 1 for each of $R_1$, $R_2$, $R_3$ and $R_4$; for example, for compound number 1, since n is 0 for each $R_1$, $R_2$, $R_3$ and $R_4$, there is no Z substituent i.e. each $R_1$, $R_2$, $R_3$ and $R_4$ is an unsubstituted benzy group.

TABLE 1

Derivatives of benzylated D-mannitol

| No | Z (for $R_1$) | Z (for $R_2$) | Z (for $R_3$) | Z (for $R_4$) | Activity (Ki) μM |
|---|---|---|---|---|---|
| 1 | (n is 0) | (n is 0) | (n is 0) | (n is 0) | 2.0 ± 0.4 |
| 2 | (n is 0) | 4-OH | 4-OH | (n is 0) | |
| 3 | (n is 0) | 3-OH | 3-OH | (n is 0) | 6.0 |
| 4 | 4-OH | 4-F | 4-F | 4-OH | 0.4 |
| 5 | 2-F | 4-OH | 4-OH | 2-F | 2.7 |
| 6 | (n is 0) | 4-OCH$_2$C$_6$H$_5$ | 4-OCH$_2$C$_6$H$_5$ | (n is 0) | <1 |
| 7 | 2-F | 4-OCH$_2$C$_6$H$_5$ | 4-OCH$_2$C$_6$H$_5$ | 2-F | |
| 8 | (n is 0) | 4-F | (n is 0) | (n is 0) | |
| 9 | (n is 0) | 4-NH$_2$ | (n is 0) | (n is 0) | 3.3 |
| 10 | 2-F | (n is 0) | (n is 0) | (n is 0) | 0.4 |
| 11 | 4-CF$_3$ | 4-CF$_3$ | 4-CF$_3$ | 4-CF$_3$ | >5 |
| 12 | 4-CN | 4-CN | 4-CN | 4-CN | 3.1 ± 0.5 |
| 13 | (n is 0) | 4-NO$_2$ | 4-NO$_2$ | (n is 0) | |
| 14 | (n is 0) | 4-CN | 4-CN | (n is 0) | 5.4 |
| 15 | (n is 0) | F$_5$ (n = 5) | F$_5$ (n = 5) | (n is 0) | >5 |
| 16 | (n is 0) | 4-F | 4-F | (n is 0) | 0.7 ± 0.2 |
| 17 | (n is 0) | 4-Cl | 4-Cl | (n is 0) | 2.0 |

TABLE 1-continued

Derivatives of benzylated D-mannitol

| No | Z (for $R_1$) | Z (for $R_2$) | Z (for $R_3$) | Z (for $R_4$) | Activity (Ki) $\mu M$ |
|---|---|---|---|---|---|
| 18 | (n is 0) | 4-Br | 4-Br | (n is 0) | 2.1 ± 0.1 |
| 19 | (n is 0) | 4-COOMe | 4-COOMe | (n is 0) | 8.4 |
| 20 | (n is 0) | 3-F | 3-F | (n is 0) | 1.8 ± 0.6 |
| 21 | (n is 0) | 2-F | 2-F | (n is 0) | 3.7 ± 0.7 |
| 22 | (n is 0) | 4-$CF_3$ | 4-$CF_3$ | (n is 0) | 10.0 |
| 23 | (n is 0) | 2,4-$F_2$ (n = 2) | 2,4-$F_2$ (n = 2) | (n is 0) | 2.6 ± 0.5 |
| 24 | (n is 0) | 4-$CH_3$ | 4-$CH_3$ | (n is 0) | 3.7 |
| 25 | (n is 0) | 2,6-$F_2$ (n = 2) | 2,6-$F_2$ (n = 2) | (n is 0) | 6.4 |
| 26 | 4-Me | (n is 0) | (n is 0) | 4-Me | 3.0 |
| 27 | 4-$CF_3$ | (n is 0) | (n is 0) | 4-$CF_3$ | >2.0 |
| 28 | 4-CN | (n is 0) | (n is 0) | 4-CN | 4.3 |
| 29 | 4-COOMe | (n is 0) | (n is 0) | 4-COOMe | 2.0 |
| 30 | 4-COO-i-Bu | (n is 0) | (n is 0) | 4-COO-i-Bu | >3.0 |
| 31 | 4-F | (n is 0) | (n is 0) | 4-F | 2.5 ± 0.5 |
| 32 | 2-F | (n is 0) | (n is 0) | 2-F | 0.6 ± 0.2 |
| 33 | 2,4-$F_2$ (n = 2) | (n is 0) | (n is 0) | 2,4-$F_2$ (n = 2) | 4.2 ± 0.5 |
| 34 | 2-F | 4-Br | 4-Br | 2-F | 1.9 ± 0.5 |
| 35 | 2,6-$F_2$ (n = 2) | (n is 0) | (n is 0) | 2,6-$F_2$ (n = 2) | 0.33 ± 0.05 |
| 36 | 2-F | 4-OMe | 4-OMe | 2-F | |
| 37 | 2-Me | 4-F | 4-F | 2-Me | |
| 38 | 2-F | 2-Me | 2-Me | 2-F | 0.8 |
| 39 | 2,6-$F_2$ | 4-F | 4-F | 2,6-$F_2$ | 0.33 ± 0.04 |
| 40 | 2-F | 4-F | 4-F | 2-F | 0.28 ± 0.03 |
| 41 | (n is 0) | 4-$NH_2$ | 4-$NH_2$ | (n is 0) | |
| 42 | 4-tert-$C_4H_9$ | 4-F | 4-F | 4-tert-$C_4H_9$ | |
| 43 | (n is 0) | 4-COOH | 4-COOH | (n is 0) | 26.0 |
| 44 | (n is 0) | 4-$CONH_2$ | 4-$CONH_2$ | (n is 0) | 20.0 |
| 45 | (n is 0) | 4-$CH_2OH$ | 4-$CH_2OH$ | (n is 0) | 10.0 |
| 46 | (n is 0) | 4-$CH_2NH_2$ | 4-$CH_2NH_2$ | (n is 0) | 27.0 |
| 47 | (n is 0) | 4-NHCOO-t-Bu | 4-NHCOO-t-Bu | (n is 0) | |
| 48 | 4-$CH_2OH$ | (n is 0) | (n is 0) | 4-$CH_2OH$ | 1.2 |
| 49 | (n is 0) | 4-CHO | 4-CHO | (n is 0) | 28.0 |
| 50 | 4-Me | 4-Me | 4-Me | 4-Me | >1.0 |
| 51 | 4-COOH | (n is 0) | (n is 0) | 4-COOH | 5.0 |
| 52 | 4-F | 4-F | 4-F | 4-F | 1.6 ± 0.2 |
| 53 | 3-F | (n is 0) | (n is 0) | 3-F | 1.5 ± 0.2 |
| 54 | 4-Br | (n is 0) | (n is 0) | 4-Br | >3.0 |
| 55 | 4-Cl | (n is 0) | (n is 0) | 4-Cl | 5.2 |
| 56 | 2-F | 4-Me | 4-Me | 2-F | 3.5 |
| 57 | 2-F | 3-F | 3-F | 2-F | 1.5 ± 0.2 |
| 58 | 4-$OCH_2C_6H_5$ | 4-F | 4-F | 4-$OCH_2C_6H_5$ | 5.0 |
| 59 | (n is 0) | 4-COOH | 4-COOMe | (n is 0) | 1.4 ± 0.1 |
| 60 | (n is 0) | 4-CN | 4-$CONH_2$ | (n is 0) | 13 |
| 61 | (n is 0) | 4-$NO_2$ | (n is 0) | (n is 0) | 23 |
| 62 | 2-F | 4-F | (n is 0) | 2-F | 0.22 |
| 63 | 2-F | 4-F | 4-F | (n is 0) | 0.89 |
| 64 | 4-$OCH_2C_6H_5$ | 4-F | 4-F | (n is 0) | |
| 65 | 3,5-$(OH)_2$ (n = 2) | 3,5-$(OH)_2$ (n = 2) | 3,5-$(OH)_2$ (n = 2) | 3,5-$(OH)_2$ (n = 2) | |
| 66 | 3,5-$(OCH_2C_6H_5)_2$ (n = 2) | 3,5-$(OCH_2C_6H_5)_2$ (n = 2) | 3,5-$(OCH_2C_6H_5)_2$ (n = 2) | 3,5-$(OCH_2C_6H_5)_2$ (n = 2) | |
| 67 | (n is 0) | 3-$OCH_2C_6H_5$ | 3-$OCH_2C_6H_5$ | (n is 0) | |
| 68 | 2-F | 4-$CH_3S$ | 4-$CH_3S$ | 2-F | |
| 69 | 4-F | 3,4-$(OH)_2$ (n = 2) | 3,4-$(OH)_2$ (n = 2) | 4-F | |
| 70 | 4-F | 3,5-$(OH)_2$ (n = 2) | 3,5-$(OH)_2$ (n = 2) | 4-F | |
| 71 | 4-F | 4-F | 4-F | 3,5-$(OCH_2C_6H_5)_2$ (n = 2) | |
| 72 | 4-F | 4-F | 4-F | 3,5$(OH)_2$ | |
| 73 | 4-F | 3,5-$(OCH_2C_6H_5)_2$ | 3,5-$(OCH_2C_6H_5)_2$ | 4-F | |
| 74 | (n = 0) | (n = 0) | 4-$NO_2$ | (n = 0) | |
| 75 | 4-F | 3,4-$(OCH_2C_6H_5)_2$ | 3,4-$(OCH_2C_6H_5)_2$ | 4-F | |
| 76 | 4-OH | 4-F | 4-F | 4-$OCH_2C_6H_5$ | 0.9 |

Table 2 shows compounds of formula 1, as defined above, wherein $R_1$, $R_2$, $R_3$, $R_4$, the same or different, each denotes a group of formula —$CH_2$—$Z_1$ wherein $Z_1$ is a substituent as shown in table 2.

TABLE 2

Tetra-substituted D-mannitol derivatives.

| No | $Z_1$ (for $R_1$) | $Z_1$ (for $R_2$) | $Z_1$ (for $R_4$) | $Z_1$ (for $R_4$) | Activity (Ki) $\mu$M |
|---|---|---|---|---|---|
| 77 | 4-pyridyl | 4-pyridyl | 4-pyridyl | 4-pyridyl | |
| 78 | vinyl | vinyl | vinyl | vinyl | 190 |
| 79 | cyclopropyl | cyclopropyl | cyclopropyl | cyclopropyl | 21 |
| 80 | phenyl | 2-naphthyl | 2-naphthyl | phenyl | >1.25 |
| 81 | H | H | H | H | |
| 82 | phenyl | vinyl | vinyl | phenyl | 11 |
| 83 | phenyl | cyclopropyl | cyclopropyl | phenyl | 9 |
| 84 | phenyl | styryl | styryl | phenyl | >1 |
| 85 | phenyl | 2-thienyl | 2-thienyl | phenyl | |
| 86 | phenyl | 4-pyridyl | 4-pyridyl | phenyl | >50 |
| 87 | phenyl | 3-pyridyl | 3-pyridyl | phenyl | |
| 88 | phenyl | 2-pyridyl | 2-pyridyl | phenyl | 28 |
| 89 | cyclopropyl | phenyl | phenyl | cyclopropyl | 16 |
| 90 | vinyl | phenyl | phenyl | vinyl | 12 |
| 91 | vinyl | 4-fluorophenyl | 4-fluorophenyl | vinyl | |
| 92 | 2-thienyl | phenyl | phenyl | 2-thienyl | 0.8 |
| 93 | 2-thienyl | 4-fluorophenyl | 4-fluorophenyl | 2-thienyl | 0.4 |
| 94 | styryl | phenyl | phenyl | styryl | >1 |
| 95 | phenethyl | 4-fluorophenyl | 4-fluorophenyl | phenethyl | |
| 96 | phenyl | 4-fluorophenyl | 2-thienyl | phenyl | 0.23 |
| 97 | 2-fluorophenyl | 4-fluorophenyl | 2-thienyl | 2-fluorophenyl | 0.23 |

Table 3 shows compounds of formula 1, as defined above, wherein $R_1$, $R_2$, $R_3$, $R_4$, each denotes a substituent as shown in table 3.

TABLE 3

Di- and tri-substituted D-mannitol derivatives.

| No | $R_1$ | $R_2$ | $R_4$ | $R_5$ | Activity (Ki) $\mu$M |
|---|---|---|---|---|---|
| 98 | benzyl | benzyl | H | benzyl | 33 |
| 99 | benzyl | 4-N02-benzyl | H | benzyl | 45 |
| 100 | phenylpropyl | 4-fluorobenzyl | H | phenylpropyl | |
| 101 | benzyl | CH$_3$S(C=S)- | CH$_3$S—(C=S)— | benzyl | >5 |
| 102 | benzyl | C$_6$H$_5$CH$_2$S(C=S)— | C$_6$H$_5$CH$_2$S—(C=S)— | benzyl | |
| 103 | 2-fluorobenzyl | 4-fluorobenzyl | CH$_3$S—(C=S)— | 2-fluorobenzyl | |
| 104 | benzyl | benzyl | CH$_3$S—(C=S)— | benzyl | |
| 105 | benzyl | benzyl | CH$_2$=CHCH$_2$S(C=S)— | benzyl | |
| 106 | benzyl | 4-fluorobenzyl | CH$_3$S—(C=S)— | phenyl | >5 |
| 107 | benzyl | benzyl | CH$_3$O—(C=O)— | phenyl | |
| 108 | phenyl | benzyl | benzyl | phenyl | |
| 109 | benzyl | benzoyl | benzoyl | benzyl | 10 |
| 110 | benzoyl | benzyl | benzyl | benzoyl | |

In the description herein, the following abbreviations are used:

| Designation | Reagent or Fragment |
|---|---|
| Et | ethyl |
| Trityl | triphenylmethyl |
| EDC | 1-(3-dimethylaminopropyl)-3-ethylcarbodiimide |
| TFA | trifluoroacetic acid |
| EtOAC | ethyl acetate |
| DMF | dimethylformamide |
| AZT | zidovudine |
| IL-2 | interleukin-2 |
| rEPO | recombinant erythropoietin |
| EtOH | ethyl alcohol |
| MeOH | methyl alcohol |
| THF | tetrahydrofuran |
| CH$_2$Cl$_2$ | dichloromethane |
| Cl$_2$-Bzl | 2,6-dichlorobenzyl |
| tert-Bu | tert-butyl |
| Bzl | benzyl |
| CHCl$_3$ | chloroform |

EXAMPLES

D-Mannitol was purchased from Aldrich CO. Canada.

The following examples are for the purpose of illustration only and are not to be construed as limiting the scope of the invention in any way. When an example relates to the preparation of a compound identified in table 1, 2, or 3 above, the compound number used in these tables will appear after the name of the compound prepared in accordance to the example.

Materials and Methods

Analytical thin layer chromatography (TLC) was carried out with 0.25 mm silica gel E. Merck 60 F$_{254}$ plates and eluted with the indicated solvent systems. Preparative chromatography was performed either by flash chromatography, using Silica Gel 60 (EM Science) with the indicated solvent systems and a positive nitrogen pressure to allow proper elution, or by thick layer chromatography, again employing E. Merck 60 F$_{254}$ plates of 0.5, 1.0, or 2.0 mm thickness. Detection of the compounds was carried out by exposing eluted plates, analytical or preparative, to UV light and treating analytical plates with a 2% p-anisaldehyde solution in ethanol containing 1% acetic acid and 3% sulfiric acid, followed by heating, unless otherwise indicated.

Nuclear magnetic resonance (NMR) spectra were recorded on a Bruker AMX 500 equipped with a reversed or QNP probe. Samples were dissolved in deuterochloroform (CDCl$_3$), deuteroacetone (acetone-d$_6$) or deuterated dimethylsulfoxide (DMSO-d$_6$) for data acquisition using tetramethylsilane (TMS) as internal standard. Chemical shifts are expressed in parts per million (ppm), the coupling constants J are expressed in hertz (Hz) and multiplicities (denoted as s for singlet, d for doublet, dd for doublet of doublets, t for triplet, q for quartet, m for multiplet, and br for broad). The number of hydrogens listed for all C$_2$-symetry compounds is half of that present in the molecule.

The following compounds were prepared from a derivative of D-mannitol using the procedures summarized in Scheme 1, 2 and 3.

Example 1
Preparation of 3,4-O-isopropylidene-D-mannitol

A suspension of D-mannitol (125 g, 687 mmol) in dry acetone (1.5 L) containing sulfuric acid (12.5 mL) was stirred at room temperature for 24 h. Neutralization with an aqueous solution of $NH_4OH$ (33%, 44 mL) and sodium carbonate (78 g) and evaporation gave a solid that was solubilized in ethanol with vigorous stirring. The mixture was filtered and concentrated to give the crude triacetonide. To the crude acetonide was added AcOH (2 L) in $H_2O$ (1 L). The reaction was heated to 40° C. for 1.5 h and then the solvent was removed in vacuo. The residue was suspended in acetone (1 L), filtered and concentrated to give a white solid. The solid was purified by recrystallization from acetone to give the desired monoacetonide (66.8%).

NMR ($CDCl_3$): 1.38 (s, 6H), 1.60 (s, 2H), 2.04 (s, 2H), 3.70–4.00 (m, 8H).

Example 2
Preparation of 1,6-di-O-benzyl-3,4-O-isopropylidene-D-mannitol

To a solution of 3,4-O-isopropylidene-D-mannitol (1 eq.), obtained as in example 1, in toluene (20 mL) was added dibutyltin oxide (2 eq.) and the mixture was heated with azeotropic removal of water for 2 h using a Dean Stark apparatus. The solvent was removed in vacuo and the resulting white solid was dissolved in DMF (10 mL). Cesium fluoride (4 eq.) was added with heating at 50° C. until the solution was homogeneous. The solution was cooled and benzyl bromide (2.2 eq.) was added in one portion. The resulting suspension was heated at 60° C. for 1 h, cooled and stirred at room temperature for an additional 16 h. The reaction mixture was diluted with saturated sodium chloride solution (20 mL) and extracted twice with EtOAc. The organic layer was dried over magnesium sulfate and concentrated in vacuo. Purification by flash chromatography eluting with 30% EtOAc in hexane yielded 65% of the title compound.

NMR ($CDCl_3$): 1.35 (s, 6H), 3.44 (m, 2H), 3.60 (m, 2H), 3.75 (d, J=3.1, 2H), 3.80 (m, 2H), 3.92 (d, J=3.0, 2H), 4.60 (s, 4H), 7.25–7.34 (m, 10H).

Example 3
Preparation of 1,2,5,6-tetra-O-benzyl-D-mannitol (compound no. 1)

To a solution of 3,4-O-isopropylidene-D-mannitol (1 eq.) as obtained from example 1 in DMF (15 mL) was added sodium hydride (6 eq.) in portions. The slurry was stirred at room temperature for 10 min. Benzyl bromide (6 eq.) dissolved in DMF (1 mL) was added dropwise. The reaction mixture was stiffed at room temperature for 12 h, then quenched by the dropwise addition of 1N HCl (10 mL). The resulting mixture was extracted twice with EtOAc. The organic layer was dried with magnesium sulfate and then concentrated. Without any further purification, the residue was stirred overnight at room temperature in 3 mL of MeOH containing 150 µL AcCl. The mixture was concentrated in vacuo and the residue was purified by flash chromatography eluting with 20% EtOAc in hexane affording a 81% yield of 1,2,5,6-tetra-O-benzyl-D-mannitol.

NMR ($CDCl_3$): 3.07 (d, J=5.5, 2H), 3.70 (dd, J=9.3, 3.7, 1H), 3.72 (m, 2H), 3.99 (t,J=5.5, 1H), 4.57 (s, 4H), 4.61 (d, J=11.2, 2H), 4.75 (d, J=11.2, 2H), 7.35 (m, 20H).

Example 4
Preparation of 1,6-di-O-benzyl-2,5-di-O-(4-cyanobenzyl)-D-mannitol (compound no. 14)

To a solution of 1,6-di-O-benzyl-3,4-O-isopropylidene-D-mannitol (1 eq.), obtained as in example 2, in DMF (10 mL) was added portionwise sodium hydride (3 eq.). After stirring 10 min, p-cyanobenzyl bromide (1 eq.) was added dropwise and the reaction mixture was stirred at room temperature for 12 h. The reaction was quenched by the addition of 1N HCl and extracted twice with EtOAc. The organic layer was dried over magnesium sulfate and the residue obtained by evaporation in vacuo was taken up in 5% HCl methanolic solution (6 mL). After 5 h of stirring at room temperature, the solvent was evaporated in vacuo and the residue was purified by flash chrlomatography using 30% EtOAc in hexane to afford 70% of the title compound.

NMR ($CDCl_3$): 3.00 (d, J=5.7, 1H), 3.67 (m, 1H), 3.86 (m, 2H), 3.96 (m, 1H), 4.54 (s, 2H), 4.65 (d, J=12.6, 1H), 4.76 (d, J=12.6, 1H, 7.20–7.60 (m, 9H).

Example 5
Preparation of 1,2,5,6-tetra-O-(4-trifluoromethylbenzyl)-D-mannitol (compound no. 11)

Following the indications found in example 3, the title compound was prepared by reacting 3,4-O-isopropylidene-D-mannitol with 4-trifluoromethyl benzyl chloride in a 72% yield.

NMR ($CDCl_3$): 3.00 (s, 1H), 3.72 (dd, J=10.3, 4.9, 1H), 3.82 (m, 2H), 4.02 (d, J=6.5, 1H), 4.60 (s, 2H), 4.68 (d, J=11.8, 1H), 4.78 (d, J=11.8, 1H), 7.42 (m, 4H), 7.56 (m, 4H).

Example 6
Preparation of 1,2,5,6-tetra-O-(4-cyanobenzyl)-D-mannitol (compound no. 12)

As described in example 3, the title compound was prepared by reacting 3,4-O-isopropylidene-D-mannitol with 4-cyanobenzyl bromide in a 65% yield.

NMR ($CDCl_3$): 2.06 (d, J=5, 1H), 3.74 (m, 1H), 3.80 (m, 2H), 4.00 (m, 1H), 4.61 (s, 2H), 4.70 (d, J=12.9, 1H), 4.82 (d, J=12.9, 1H), 7.40 (m, 4H), 7.60 (m, 4H).

Example 7
Preparation of 1,2,5,6-tetra-O-(4-methylbenzyl)-D-mannitol (compound no. 50)

As described in example 3, the title compound was prepared by reacting 3,4-O-isopropylidene-D-mannitol with 4-methylbenzyl bromide in a 65% yield.

NMR ($CDCl_3$): 2.30 (s, 3H), 2.31 (s, 3H), 2.99 (br, 1H), 3.63 (dd, J=5.1, 10.2, 1H), 3.72 (m, 2H), 3.93 (d, J=6.4, 1H), 4.48 (s, 2H), 4.51 (d, J=11.3, 1H), 4.65 (d, J=11.3, 1H), 7.07 (d, J=8.3, 2H), 7.09 (d, J=8.9, 2H), 7.18 (d, J=7.8, 2H), 7.19 (d, J=7.5, 2H).

Example 8
Preparation of 1,2,5,6-tetra-O-(3,5-dihydroxybenzyl)-D-mannitol (compound no. 65)

Step A. 1,2,5,6-tetra-O-(3,5-dibenzyloxybenzyl)-3,4-O-isopropylidene-D-mannitol (compound no. 66)

As described in example 3, the title compound was prepared by reacting 3,4-O-isopropylidene-D-mannitol with 3,5-dibenzyloxybenzyl chloride providing the desired 1,2,5,6-tetra-O-3,5-dibenzyloxybenzyl)-D-mannitol in a 9% yield.

NMR ($CDCl_3$): 1.37 (s, 3H), 3.61–3.64 (m, 1H), 3.74–3.79 (m, 2H), 4.39 (s, 2H), 4.55 (d, J=12.3, 1H), 4.70 (d, J=11.7, 1H), 4.81–4.89 (m, 3H), 6.42 (s, 2H), 6.47 (s, 1H), 6.55 (s, 2H), 6.59 (s, 2H), 7.26–7.32 (m, 2H).

Step B. 1,2,5,6-tetra-O-(3,5-dihydroxybenzyl)-D-mannitol

The product obtained in step A of this example was hydrogenolyzed in EtOAc containing 5% palladium on charcoal and one drop of pyridine. Purification of the crude product by flash chromatography eluting with 15% MeOH in $CH_2Cl_2$ provided the desired product (29%).

NMR ($CDCl_3$): 3.67–3.77 (m, 6H), 3.89 (d, J=9.9, 2H), 3.98 (d, J=6.8, 2H), 4.48–4.57 (m, 6H), 4.65 (d, J=11.8, 2H), 6.28 (s, 2H), 6.38 (s, 2H), 7.06 (t, J=8.4, 4H), 7.39 (t, J=6.1, 4H), 8.14 (s, 4H).

Example 9

Preparation of 1,2,5,6-tetra-O-(4-fluorobenzyl)-D-mannitol (compound no. 52)

As described in example 3, the title compound was prepared by reacting 3,4-O-isopropylidene-D-mannitol with 4-fluorobenzyl bromide in a 73% yield.

NMR ($CDCl_3$): 3.00 (d, J=5.8, 1H), 3.59–3.67 (m, 1H), 3.69–3.80 (m, 2H), 3.90 (t, 4.0, 1H), 4.50 (s, 2H), 4.58 (d, J=11.3, 1H), 4.68 (d, J=11.3, 1H), 6.90–7.05 (m, 4H), 7.20–7.34 (m, 4H).

Example 10

1,2,5,6-tetra-O-(4-pyridylmethyl)-D-mannitol (compound no. 77)

As described in example 3, the title compound was prepared by reacting 3,4-O-isopropylidene-D-mannitol with 4-pyridylmethyl chloride hydrochloride in a 10% yield.

NMR ($CDCl_3$): 2.30 (s, 1H), 3.68 (dd, J=7.1, 11.1, 1H), 3.80 (d, J=9.2, 2H), 4.22 (d, J=3.5, 1H), 4.50 (s, 2H), 4.60 (d, J=13.1, 1H), 4.80 (d, J=13.4, 1H), 7.20 (d, J=7.19 (d, J=5.3, 2H), 7.22 (d, J=5.3, 2H), 8.51 (d, J=5.1, 2H), 8.53 (d, J=5.1, 2H).

Example 11

1,2,5,6-tetra-O-allyl-D-mannitol (compound no. 78)

As described in example 3, the title compound was prepared by reacting 3,4-O-isopropylidene-D-mannitol with allyl bromide in a 50% yield.

NMR ($CDCl_3$): 3.10 (br, 1H), 3.60–3.75 (m, 3H), 3.88 (d, J=5.8, 1H), 4.02 (d, J=5.5 2H), 4.10 (m, 1H), 4.22 (m, 1H), 5.17 (t, J=11.1, 2H), 5.27 (dd, J=8.5, 17.3, 2H), 5.93 (m, 2H).

Example 12

1,2,5,6-tetra-O-methyl-D-mannitol (compound no. 81)

As described in example 3, the title compound was prepared by reacting 3,4-O-isopropylidene-D-mannitol with methyl iodide in a 15% yield.

NMR ($CDCl_3$): 1.54 (br, 1H), 3.31 (s, 3H), 3.42 (s, 3H), 3.40–3.48 (m, 1H), 3.58 (dd, J=7.4, 10.5, 1H), 4.04 (m, 1H).

Example 13

1,2,5,6-tetra-O-cyclopropylmethyl-D-mannitol (compound no. 79)

As described in example 3, the title compound was prepared by reacting 3,4-O-isopropylidene-D-mannitol with cyclopropylmethyl bromide in a 45% yield.

NMR (DMSO-$d_6$): 0.15 (m, 4H), 0.43 (m, 4H), 0.97 (d, J=6.4, 2H), 3.20–3.40 (m, 6H), 3.55 (d, J=8.5, 1H), 3.71 (d, J=10.4, 1H), 4.22 (br, 1H).

Example 14

Preparation of 1,6-di-O-benzyl-2,5-di-O-(4-carbomethoxybenzyl)-D-mannitol (compound no. 19)

As described in example 4, the title compound was prepared by reacting 1,6-di-O-benzyl-3,4-O-isopropylidene-D-mannitol with 4-trifluoromethylbenzyl bromide in a 75% yield.

NMR ($CDCl_3$): 3.04 (d, J=5.8, 1H), 3.68 (m, 1H), 3.75 (m, 2H), 3.90 (s, 3H), 4.00 (m, 1H), 4.52 (s, 2H), 4.64 (d, 12.5, 1H), 4.77 (d, J=12.3, 1H), 7.25 (m, 5H), 7.36 (d, J=7.7, 2H), 7.98 (d, J=7.8, 2H).

Example 15

Preparation of 1,6-di-O-benzyl-2,5-di-O-(4-benzyloxybenzyl)-D-mannitol (compound no. 6)

As described in example 4, the title compound was prepared by reacting 1,6-di-O-benzyl-3,4-O-isopropylidene-D-mannitol with 4-benzyloxybenzyl chloride in a 62% yield.

NMR ($CDCl_3$): 3.02 (d, J=6.3, 1H), 3.65 (dd, J=10.9, 5.2, 1H), 3.73 (m, 2H), 3.93 (t, J=6.2, 1H), 4.51 (d, J=11.2, 1H), 4.54 (s, 2H), 4.64 (d, J=11.2, 1H), 5.03 (s, 2H), 6.90 (d, J=7.4, 2H), 7.22 (d, J=8.6, 2H), 7.25–7.44 (m, 10H).

Example 16

Preparation of 1,6-di-O-benzyl-2,5-di-O-(4-hydroxybenzyl)-D-mannitol (compound no. 2)

A mixture of 1,6-di-O-benzyl-2,5-di-O-(4-benzyloxybenzyl)-D-mannitol, obtained as in example 15, (97 mg, 0.10 mmol) in MeOH (1 mL), pyridine (8.0 mg, 0.1 mmol) and 5% palladium on charcoal (70 mg) was hydrogenated at normal pressure and room temperature for 1 h. The reaction mixture was filtered and concentrated in vacuo. Flash chromatography on silica gel eluting with 50% EtOAc in hexane afforded the title compound in 87% yield.

NMR ($CDCl_3$): 3.45 (d, J=5.3, 1H), 3.64 (dd, J=11.4, 5.5, 1H), 3.71 (d, J=5.2, 1H), 3.75 (dd, J=11.2, 5.5, 1H), 4.00 (t, J=5.3, 1H), 4.40 (d, J=5.3, 1H), 4.52 (s, 2H), 4.60 (d, J=11.0, 1H), 6.37 (s, 1H), 6.62 (d, J=7.5, 2H), 7.06 (d, J=7.5, 2H), 7.30 (m, 5H).

Example 17

Preparation of 1,6-dibenzyl-2,5-di-(3-benzyloxybenzyl)-mannitol (compound no. 67)

As described in example 4, the title compound was prepared by reacting 1,6-di-O-benzyl-3,4-O-isopropylidene-D-mannitol with 3-benzyloxybenzyl bromide in a 62% yield.

NMR ($CDCl_3$): 3.02 (d, J=5.0, 1H), 3.68 (dd, J=6.0, 11.0, 1H), 3.74 (d, J=7.7, 2H), 3.97 (t, J=5.0, 1H), 4.50 (s, 2H), 4.60 (d, J=11.0, 1H), 4.70 (d, J=11.0, 1H), 5.03 (s, 2H), 6.90–7.40 (m, 14H).

Example 18

Preparation of 1,6-di-O-benzyl-2,5-di-O-(4-trifluoromethylbenzyl)-D-mannitol (compound no. 22)

As described in example 4, the title compound was prepared by reacting 1,6-di-O-benzyl-3,4-O-isopropylidene-D-mannitol with 4-trifluoromethylbenzyl bromide in a 76% yield.

NMR ($CDCl_3$): 3.05 (d, J=5.5, 1H), 3.67 (m, 1H), 3.77 (m, 2H), 4.00 (s, 1H), 4.54 (s, 2H), 4.65 (d, J=12.4, 1H), 4.77 (d, J=11.9, 1H), 7.25–7.40 (m, 9H).

Example 19

Preparation of 1,6-di-O-benzyl-2,5-di-O-(4-methylbenzyl)-D-mannitol (compound no. 24)

As described in example 4, the title compound was prepared by reacting 1,6-di-O-benzyl-3,4-O-isopropylidene-D-mannitol with 4-methylbenzyl bromide in a 89% yield.

NMR ($CDCl_3$): 2.31 (s, 3H), 3.00 (s, 1H), 3.64 (m, 1H), 3.74 (m, 2H), 3.90 (s, 1H), 4.53 (s, 2H), 4.54 (d, J=10.7, 1H), 4.67 (d, J=11.2, 1H), 7.10–7.35 (m, 9H).

Example 20

Preparation of 1,6-di-O-benzyl, 2,5-di-O-(4-bromobenzyl)-D-mannitol (compound no. 18)

As described in example 4, the title compound was prepared by reacting 1,6-di-O-benzyl-3,4-O-isopropylidene-D-mannitol with 4-bromobenzyl bromide in a 82% yield.

NMR (CDCl$_3$): 3.02 (d, J=5.6, 1H), 3.65 (m, 1H), 3.72 (d, J=7.2, 2H), 3.93 (t, J=6.1, 1H), 4.51 (d, J=7.4, 1H), 4.53 (s, 2H), 4.64 (d, J=12.2, 1H), 7.15 d, J=7.7, 2H), 7.30 (m, 5H), 7.40 (d, J=7.7, 2H).

Example 21

Preparation of 1,6-di-O-benzyl-2,5-di-O-(4-chlorobenzyl)-D-mannitol (compound no. 17)

As described in example 4, the title compound was prepared by reacting 1,6-di-O-benzyl-3,4-O-isopropylidene-D-mannitol with 4-chlorobenzyl bromide in a 85% yield.

NMR (CDCl$_3$): 3.08 (br, 1H), 3.61 (m, 1H), 3.70–3.81 (m, 2H), 4.50 (s, 2H), 4.54 (d, J=11.5, 1H), 4.68 (d, J=11.5, 1H), 7.10–7.42 (m, 9H).

Example 22

Preparation of 1,6-di-O-benzyl-2,5-di-O-(4-fluorobenzyl)-D-mannitol (compound no. 16)

As described in example 4, the title compound was prepared by reacting 1,6-di-O-benzyl-3,4-O-isopropylidene-D-mannitol with 4-fluorobenzyl bromide in a 71% yield.

NMR (CDCl$_3$): 3.01 (d, J=4.5, 1H), 3.63 (m, 1H), 3.75 (m, 2H), 3.93 (t, J=5.1, 1H), 4.53 (s, 2H), 4.54 (d, J=11.5, 1H), 4.66 (d, J=11.7, 1H), 6.99 (m, 4H), 7.25 (m, 5H).

Example 23

Preparation of 1,6-di-O-benzyl-2,5-di-O-(2,6-difluorobenzyl)-D-mannitol (compound no. 25)

As described in example 4, the title compound was prepared by reacting 1,6-di-O-benzyl-3,4-O-isopropylidene-D-mannitol with 2,6-difluorobenzyl bromide in a 92% yield.

NMR (CDCl$_3$): 2.94 (d, J=5.5, 1H), 3.66 (dd, J=10.1, 5.5, 1H), 3.77 (m, 2H), 3.88 (t, J=6.5, 1H), 4.56 (s, 2H), 4.66 (d, J=10.8, 1H), 4.86 (d, J=11.0, 1H), 6.85 (m, 2H), 7.30 (m, 6H).

Example 24

Preparation of 1,6-di-O-benzyl-2,5-di-O-(2,4-difluorobenzyl)-D-mannitol (compound no. 23)

As described in example 4, the title compound was prepared by reacting 1,6-di-O-benzyl-3,4-O-isopropylidene-D-mannitol with 2,4-difluorobenzyl bromide in a 88% yield.

NMR (CDCl$_3$): 2.97 (d, J=5.8, 1H), 3.67 (dd, J=11.1, 6.6, 1H), 3.75 (d, J=7.4 2H), 3.91 (dd, J=6.2, 11.5, 1H), 4.55 (s, 2H), 4.60 (d, J=12.0, 1H), 4.73 (d, J=11.8, 1H), 6.79 (m, 2H), 7.31 (m, 6H).

Example 25

Preparation of 1,6-di-O-benzyl-2,5-di-O-(2-fluorobenzyl)-D-mannitol (compound no. 21)

As described in example 4, the title compound was prepared by reacting 1,6-di-O-benzyl-3,4-O-isopropylidene-D-mannitol with 2-fluorobenzyl bromide in a 93% yield.

NMR (CDCl$_3$): 3.02 (d, J=5.6, 1H), 3.69 (dd, J=10.9, 5.4, 1H), 3.78 (m, 2H), 3.95 (t, J=6.1, 1H), 4.54 (s, 2H), 4.65 (d, J=11.7, 1H), 4.78 (d, J=11.9, 1H), 7.00 (t, J=9.3, 1H), 7.07 (t, J=7.5, 1H), 7.27 (m, 1H), 7.31 (s, 5H), 7.36 (m, 1H).

Example 26

Preparation of 1,6-di-O-benzyl-2,5-di-O-(3-fluorobenzyl)-D-mannitol (compound no. 20)

As described in example 4, the title compound was prepared by reacting 1,6-di-O-benzyl-3,4-O-isopropylidene-D-mannitol with 3-fluorobenzyl bromide in a 85% yield.

NMR (CDCl$_3$): 3.05 (d, J=5.6, 1H), 3.67 (dd, J=13.1, 7.2, 1H), 3.75 (m, 6.9, 2H), 3.96 (t, J=5.9, 1H), 4.54 (s, 2H), 4.58 (d, J=11.5, 1H), 4.70 (d, J=11.5, 1H), 6.93 (m, 1H), 7.03 (m, 2H), 7.28 (m, 1H), 7.30 (s, 5H).

Example 27

Preparation of 1,6-di-O-benzyl-2,5-di-O-(pentafluorobenzyl)-D-mannitol (compound no. 15)

As described in example 4, the title compound was prepared by reacting 1,6-di-O-benzyl-3,4-O-isopropylidene-D-mannitol with pentafluorobenzyl bromide in a 23% yield.

NMR (CDCl$_3$): 2.85 (d, J=5.5, 1H), 3.62 (m, 1H), 3.77 (m, 2H), 3.81 (t, J=5.3, 1H), 4.54 (s, 2H), 4.67 (d, J=11.1, 1H), 4.82 (d, J=10.9, 1H), 7.30 (m, 5H).

Example 28

Preparation of 1,2,5-tri-O-(4-fluorobenzyl)-6-O-(3,5-dihydroxybenzyl)-D-mannitol (compound no. 72)

Step A. 1-O-(3,5-dibenzyloxybenzyl)-O-3,4-isopropylidene-D-mannitol

Following the indications of example 2, but carrying out the reaction with 3,5-dibenzyloxybenzyl chloride at room temperature instead of 60° C., the monoalkylated manntol derivative was isolated in 29% yield after purification by flash chromatography eluting with 50% EtOAc in hexane.

NMR (CDCl$_3$): 1.38 (s, 6H), 3.57–3.95 (m, 10H), 4.54 (d, J=5.8, 2H), 5.04 (s, 4H), 6.58 (s, 1H), 6.62 (s, 2H), 7.34–7.44 (m, 10H).

Step B. 1,2,5-tri-O-4-fluorobenzyl)-6-O-(3,5-dibenzyloxybenzyl)-D-mannitol (compound no. 71)

The product of step A of this example was alkylated with 4-fluorobenzyl bromide using the conditions described in example 3. Purification by flash chromatography eluting with 30% EtOAc in hexane provided 50% of the desired product.

NMR (CDCl$_3$): 3.61–3.74 (m, 8H), 3.76 (t, J=5.4, 2H), 4.47 (d, J=6.8, 4H), 4.52–4.55 (m, 2H), 4.66 (t, J=12.2, 2H), 4.78 (s, 4H), 6.58 (s, 2H), 6.96 (q, J=8.9, 6H), 7.23–7.39 (m, 7H).

Step C. 1,2,5-tri-O-4-fluorobenzyl)-6-O-(3,5-dihydroxybenzyl)-D-mannitol

The product of step B of this example was hydrogenolyzed using 5% palladium on charcoal in methanol and in the presence of pyridine. Filtration and evaporation to dryness left a residue that was purified by flash chromatography eluting with 50% EtOAc in hexane. The title compound (73%) was thus obtained.

NMR (CDCl$_3$): 3.22 (d, J=6.5, 1H), 3.26 (s, 1H), 3.56–3.71 (m, 5H), 3.79 (d, J=4.5, 1H), 4.01 (s, 1H), 4.06 (s, 1H), 4.29 (d, J=12.5, 1H), 4.40 (d, J=13.0, 1H), 4.44–4.53 (m, 4H), 4.60 (dd, J=4.0, 11.0, 2H), 6.2 (s, 1H), 6.29 (s, 2H), 6.48 (s, 2H), 6.94 (q, J=9.0, 6H), 7.21–7.25 (m, 6H).

Example 29

Preparation of-1,6-di-O-(4-carboisobutoxybenzyl)-2,5-di-O-benzyl D-mannitol (compound no. 30)

The alkylation of 3,4-O-isopropylidene-D-mannitol with 4-carboisobutoxybenzyl bromide was carried out as described in example 2. The resulting 1,6-di-O-(4-carboisobutoxybenzyl)-3,4-O-isopropylidene-D-mannitol was not characterized but reacted with benzyl bromide according to the conditions described in example 4. Purification by flash chromatography provided a 56% yield.

NMR (CDCl$_3$): 1.01 (d, J=7.3, 6H), 2.08 (h, J=7.3, 1H), 2.96 (d, J=5.5, 1H), 3.65 (m, 1H), 3.75 (m, 2H), 3.97 (t, J=5.8, 1H), 4.10 (d, J=7.3, 2H), 4.58 (s, 2H), 4.61 (d, J=11.8, 1H), 4.73 (d, J=11.1, 1H), 7.30 (m, 5H), 7.37 (d, J=8.6, 2H), 7.99 (d, J=7.8, 2H).

Example 30

Preparation of 1,6-di-O-(3-fluorobenzyl)-2,5-di-O-(benzyl)-D-mannitol (compound no 53)

The alkylation of 3,4-O-isopropylidene-D-mannitol with 3-fluorobenzyl bromide was carried out as described in example 2. The resulting 1,6-di-O-(3-fluorobenzyl)-3,4-O-isopropylidene-D-mannitol was not characterized but reacted with benzyl bromide according to the conditions described in example 6. Purification by flash chromatography provided a 63% yield.

NMR (CDCl$_3$): 3.08 (d, J=7.0, 1H), 3.65 (d, J=11.2, 1H), 3.65–3.70 (m, 1H), 3.72–3.80 (m, 2H), 3.80 (d, J=11.2, 1H), 4.00 (t, J=4.3, 1H), 4.50 (s, 2H), 7.29–7.56 (m, 8H).

Example 31
Preparation of 1,6-di-O-(2-fluorobenzyl)-2,5-di-O-(3-fluorobenzyl)-D-mannitol (compound no. 57)

The alkylation of 3,4-O-isopropylidene-D-mannitol with 2-fluorobenzyl bromide was carried out as described in example 2. The resulting 1,6-di-O-(2-fluorobenzyl)-3,4-O-isopropylidene-D-mannitol was not characterized but reacted with 3-fluorobenzy bromide according to the conditions described in example 4. Purification by flash chromatography provided a 58% yield.

NMR (CDCl$_3$): 3.02 (d, J=6.0, 1H), 3.65–3.70 (m, 1H), 3.71–3.80 (m, 2H), 3.90 (s, 1H), 4.50 (s, 2H), 4.50 (d, J=11.1, 1H), 4.65 (d, J=11.1, 1H), 6.88–7.40 (m, 8H).

Example 32
Preparation of 1,6-di-O-(2,6-difluorobenzyl)-2,5-di-O-benzyl-D-mannitol (compound no. 35)

The alkylation of 3,4-O-isopropylidene-D-mannitol with 2,6-difluorobenzyl bromide was carried out as described in example 2. The resulting 1,6-di-O-(2,6-difluorobenzyl)-3,4-O-isopropylidene-D-mannitol was not characterized but reacted with benzyl bromide according to the conditions described in example 6. Purification by flash chromatography provided a 56% yield.

NMR (CDCl$_3$): 2.95 (d, J=4.0, 1H), 3.68 (m, 2H), 3.78 (m, 1H), 3.87 (m, 1H), 4.55 (d, J=11.0, 1H), 4.61 (d, J=11.0, 1H), 4.65 (d, J=11.0, 1H), 4.70 (d, J=11.0, 1H), 6.88 (m, 2H), 7.29 (m, 6H).

Example 33
Preparation of 1,6-di-O-benzyl-2,5-di-O-(2-naphthylmethyl)-D-mannitol (compound no. 80)

As described in example 4, the title compound was prepared by reacting 1,6-di-O-benzyl-3,4-O-isopropylidene-D-manntol with 2-naphthyhnethyl bromide in a 88% yield.

NMR (CDCl$_3$): 3.09 (d, J=5.8, 1H), 3.68 (m, 1H), 3.77 (m, 2H), 4.03 (t, J=6.1, 1H), 4.54 (s, 2H), 4.74 (d, J=7.4, 1H), 4.86 (d, J=11.8, 1H, 7.20–7.80 (m, 12H).

Example 34
Preparation of 1,6-di-O-benzyl-2,5-di-O-allyl-D-mannitol (compound no. 82)

As described in example 4, the title compound was prepared by reacting 1,6-di-O-benzyl-3,4-O-isopropylidene-D-mannitol with allyl bromide in a 23% yield.

NMR (CDCl$_3$): 3.11 (d, J=5.4, 1H), 3.65 (m, 3H), 3.91 (t, J=5.2, 1H), 4.08 (dd, J=12.6, 5.8, 1H), 4.20 (dd, J=12.5, 5.4, 1H), 4.55 (s, 2H), 5.14 (d, J=10.3, 1H), 5.22 (d, J=17.4, 1H, 5.90 (m, 1H), 7.30 (m, 5H).

Example 35
Preparation of 1,6-di-O-benzyl-2,5-di-O-cyclopropylmethyl-D-mannitol (compound no. 83)

As described in example 4, the title compound was prepared by reacting 1,6-di-O-benzyl-3,4-O-isopropylidene-D-mannitol with cyclopropylmethyl bromide in a 76% yield.

NMR (CDCl$_3$): 0.18 (d, J=4.7, 2H), 0.50 (d, J=7.5, 2H), 1.04 (m, 1H), 3.26 (d, J=5.4, 1H), 3.39 (m, 1H), 3.50 (m, 1H), 3.65 (m, 2H), 3.90 (m, 1H), 4.56 (s, 2H), 7.33 (m, 5H).

Example 36
Preparation of 1,6-di-O-benzyl, 2,5-di-O-cinnamyl-D-mannitol (compound no. 84)

As described in example 4, the title compound was prepared by reacting 1,6-di-O-benzyl-3,4-O-isopropylidene-D-mannitol with cinnamyl bromide in a 77% yield.

NMR (CDCl$_3$): 3.17 (d, J=5.5, 1H), 3.68 (m, 1H), 3.76 (d, J=6.5, 2H), 3.98 (t, J=5.5, 1H), 4.26 (dd, J=12.4, 5.8, 1H), 4.35 (dd, J=12.5,5.9, 1H), 4.56 (s, 2H), 6.27 (m, 1H), 6.58 (d, J=15.7, 1H), 7.21–7.36 (m, 10H).

Example 37
Preparation of 1,6-di-O-benzyl-2,5-di-O-(2-thienylmethyl)-D-mannitol (compound no. 85)

As described in example 4, the title compound was prepared by reacting 1,6-di-O-benzyl-3,4-O-isopropylidene-D-mannitol with 2-thienylmethyl bromide in a 53% yield.

NMR (CDCl$_3$): 2.94 (d, J=6.0, 1H), 3.64 (dd, J=14.0, 9.0, 1H), 3.75 (m, 2H), 3.90 (t, J=8.0, 1H), 4.55 (s, 2H), 4.76 (d, J=15.0, 1H), 4.90 (d, J=11.5, 1H), 6.90–7.30 (m, 9H).

Example 38
Preparation of 1,6-di-O-benzyl-2,5-di-O-(4-pyridylmethyl)-D-mannitol (compound no. 86)

As described in example 4, the title compound was prepared by reacting 1,6-di-O-benzyl- 3,4-O-isopropylidene-D-mannitol with 4-pyridylmethyl chloride hydrochloride in a 23% yield.

NMR (CDCl$_3$): 3.30 (br, 1H), 3.72 (m, 1H), 3.79 (m, 3H), 4.00 (d, J=6.2, 1H), 4.54 (s, 2H), 4.60 (d, J=13.0, 1H), 4.74 (d, J=13.1, 1H), 7.18 (d, J=4.5, 2H), 7.30 (s, 5H), 8.50 (d, J=4.5, 2H).

Example 39
Preparation of 1,6-di-O-benzyl-2,5-di-O-(3-pyridylmethyl)-D-mannitol (compound no. 87)

As described in example 4, the title compound was prepared by reacting 1,6-di-O-benzyl-3,4-O-isopropylidene-D-mannitol with 3-pyridylmethyl chloride hydrochloride in a 25% yield.

NMR (CDCl$_3$): 3.00 (br, 1H), 3.68 (dd, J=5.5, 10.0, 1H), 3.77 (m, 2H), 3.94 (d, J=5.5, 1H), 4.54 (s, 2H), 4.60 (d, J=12.0, 1H), 4.73 (d, J=12.0, 1H), 7.20–7.35 (m, 6H), 7.63 (d, J=7.5, 1H), 8.52 (d, J=5.5, 2H).

Example 40
Preparation of 1,6-di-O-benzyl-2,5-di-O-(2-pyridylmethyl)-D-mannitol (compound no. 88)

As described in example 4, the title compound was prepared by reacting 1,6-di-O-benzyi-3,4-O-isopropylidene-D-mannitol with 2-pyridylmethyl chloride hydrochloride in a 15% yield.

NMR (CDCl$_3$): 3.78 (dd, J=6.0, 10.7, 1H), 3.95 (d, J=8.7, 1H), 4.06 (d, J=7.5, 1H), 4.57 (s, 2H), 4.86 (d, J=13.8, 1H), 4.93 (d, J=13.8, 1H), 7.17, (t, J=7.0, 1H), 7.20–7.35 (m, 6H), 7.63 (d, J=6.5, 1H), 8.51 (d, J=4.7, 2H).

Example 41
Preparation of 1,6-di-O-benzyl-2,5-di-O-(4-aminobenzyl)-D-mannitol (compound no. 41)

To a solution of 1,6-di-O-benzyl-2,5-di-O-(4-nitrobenzyl)-D-mannitol (64 mg, 0.1 mmol) prepared in example 74 in MeOH was added 5% palladium on charcoal (40 mg) and sodium borohydride (114 mg, 3.0 mmol). The reaction mixture was stirred at room temperature for 2 h. Saturated sodium chloride (2 mL) was added and stirring was continued for 5 h. The mixture was extracted with EtOAc, dried over magnesium sulfate and concentrated in vacuo to yield (44 mg, 85%) after purification by flash chromatography.

NMR (CDCl$_3$): 3.04 (br, 1H), 3.61 (m, 1H), 3.70 (m, 2H), 3.90 (d, J=5.9, 1H), 4.43 (d, J=11.0, 1H), 4.53 (s, 2H), 4.60 (d, J=11.0, 1H), 6.57 (d, J=8.3, 2H), 7.08 (d, J=8.1, 2H), 7.30 (s, 5H).

Example 42
Preparation of 1,6-di-O-benzyl-2,5-di-O-(4-tert-butyloxycarbonylaminobenzyl)-D-monnitol (compound no. 42)

To a solution of 1,6-di-O-benzyl-2,5-di-O-(4-aminobenzyl)-D-mannitol (320 mg, 0.5 mmol) from example 38 in EtOAc (2 mL) was added triethylamine (50 mg, 2.5 mmol) and 2-(tert-butoxycarbonyloxyamino)-2-phenylacetonitrile (BOC-ON) (500 mg, 2.5 mmol). The mixture was stirred for 24 h at room temperature. The mixture was evaporated in vacuo and the residue was purified by flash chromatography eluting with 30% EtOAc in hexane, yielding the title compound in 92% yield.

NMR (CDCl$_3$): 1.52 (s, 9H), 3.00 (d, J=5.5, 1H), 3.62 (dd, J=11.0, 5.5, 1H), 3.71 (m, 2H), 3.91 (m, 1H), 4.50 (m, 3H), 4.66 (d, J=11.0, 1H), 6.53 (s, 1H), 7.10 (d, J=8.0, 2H), 7.32 (m, 7H).

Example 43
Preparation of 1,6-di-O-benzyl-2,5-di-O-(4-carboxamidobenzyl)-D-mannitol (compound no. 44)

To a suspension of 1,6-di-O-benzyl-2,5-di-O-(4-cyanobenzyl)-D-mannitol (100 mg, 0.17 mmol) (prepared in example 4) in ethanol (1 mL) was added 1N sodium hydroxide (0.5 mL) and the mixture was refluxed for 3 h and then cooled to 0° C. 1N HCl was added dropwise until the pH of the mixture was acid. The reaction mixture was extracted with EtOAc, dried over magnesium sulfate and concentrated in vacuo. The crude material was purified by flash chrlomatography eluting with 5% MeOH in methylene chloride to yield 78% of the title compound. In addition, another fraction was found to be 1,6-di-O-benzyl-2-O-(4-cyanobenzyl)-5-O-(4-carboxamidobenzyl)-D-marmitol (7%).

1,6-di-O-benzyl-2-O-(4-cyanobenzyl)-5-O-(4-carboxamidobenzyl)-D-mannitol (compound no. 60)

NMR (CDCl3): 3.13 (d, J=6.0, 1H), 3.16 (d, J=8.5, 1H), 3.68–3.72 (m, 2H), 3.73–3.82 (m, 4H), 4.10–4.14 (m, 2H), 4.54 (s, 2H), 4.55 (s, 2H), 4.63 (d, J=13.0, 2H), 4.77 (d, J=13.0, 2H), 5.90 (br, 4H), 6.10 (br, 1H), 7.28–7.42 (m, 14H), 7.55 (d, J=7.5, 2H), 7.72 (d, J=7.0, 2H).

1,6-di-O-benzyl-2,5-di-O-(4-carboxamidobenzyl)-D-mannitol

NMR (DMSO-d$_6$): 2.51 (s, 1H), 3.62 (m, 1H), 3.68 (m, 1H), 3.80 (d, J=6.0, 1H), 3.89 (d, J=6.0, 1H), 4.50 (s, 2H), 4.60 (d, J=12.0, 1H), 7.30 (m, 5H), 7.38 (d, J=7.8, 2H), 7.81 (d, J=7.8, 2H), 7.92 (s, 1H).

Example 44
Preparation of 1,6-di-O-benzyl-2,5-di-O-(4-aminomethylbenzyl)-D-mannitol (compound no. 46)

A stirred solution of 1,6-di-O-benzyl-2,5-di-O-(4-cyanobenzyl)-D-mannitol (100 mg, 0.17 mmol) (prepared in example 4) and lithium aluminum hydride (32 mg, 0.85 mmol) was heated at reflux for 3 h in THF. After cooling at room temperature, the reaction was treated with 2N sodium hydroxide and stirring was continued for a period of 5 h. The mixture was extracted with EtOAc and the extract was dried over magnesium sulfate and concentrated in vacuo. After purification by flash chrlomatography eluting with 10% MeOH in methylene chloride, the title compound was obtained in 37% yield.

NMR (CDCl$_3$): 1.80 (br, 1H), 3.04 (br, 1H), 3.64 (m, 1H), 3.95 (m, 1H), 4.15 (m, 2H), 4.53 (s, 2H), 4.55 (d, J=12.0, 1H), 4.66 (d, J=12.0, 1H), 5.00 (s, 2H), 7.30–7.42 (m, 9H).

Example 45
Preparation of 1,6-di-O-benzyl-2,5-di-O-(4-carboxybenzyl)-D-mannitol (compound no. 43)

To a solution of 1,6-di-O-benzyl-2,5-di-O-(4-carbomethoxybenzyl)-D-mannitol, obtained as in example 14, (65 mg, 0.1 mmol) in MeOH (2 mL) and water (1 mL) was added sodium hydroxide (16 mg, 0.4 mmol). The reaction was stirred at room temperature for 3 h. 10% HCl was then added and the mixture was extracted with EtOAc. The organic layer was dried over magnesium sulfate and concentrated in vacuo. The residue was purified by flash chromatography eluting with 10% MeOH in methylene chloride to yield 77% of the desired title compound. In addition, 1,6-di-O-benzyl-2-O-(4-carboxybenzyl)-5-O-(4-carbomethoxybenzyl)-D-mannitol was obtained in a low yield of 5%.

1,6-di-O-benzyl-2-O-(4-carboxybenzyl)-5-O-(4-carbomethoxybenzyl)-D-mannitol (compound no. 59)

NMR (DMSO-d$_6$): 2.58 (s, 1H), 3.70 (m, 1H), 3.77 (t, J=5.0, 1H), 3.85 (s, 1H), 4.02 (d, J=11.0, 1H), 4.60 (s, 2H), 4.70 (d, J=11.0, 1H), 4.88 (d, J=11.0, 1H), 7.35–7.40 (m, 9H), 8.12 (d, J=8.0, 1H).

1,6-di-O-benzyl-2,5-di-O(4-carboxybenzyl)-D-mannitol

NMR (DMSO-d$_6$): 2.60 (s, 1H), 3.70 (m, 1H), 3.79 (t, J=5.0, 1H), 3.88 (s, 1H), 4.00 (d, J=11.0, 1H), 4.62 (s, 2H), 4.68 (d, J=11.0, 1H), 4.88 (d, J=1.0, 1H), 7.40 (m, 9H), 8.10 (d, J=8.0, 1H).

Example 46
Preparation of 1,6-di-O-benzyl-2,5-di-O-(4-hydroxymethylbenzyl)-D-mannitol (compound no. 45)

In a similar fashion as described in example 44, using 1,6-dibenzyl-2,5-di-O-(4-carbomethoxybenzyl)-D-mannitol, obtained as in example 14, in place of 1,6-di-O-benzyl-2,5-di-O-(4-cyanobeny)-D-mannitol, was reduced to the desired product with lithium aluminium hydride in 88% yield.

NMR (CDCl$_3$): 3.04 (br, 1H), 3.66 (m, 1H), 3.75 (m, 2H), 3.94 (m, 1H), 4.54 (s, 2H), 4.57 (d, J=12.3 1IH), 4.65 (s, 2H), 4.71 (d, J=11.5, 1H), 7.30 (m, 9H).

Example 47
Preparation of 1,6-di-O-benzyl-2,5-di-O-(4-formylbenzyl)-D-mannitol (compound no. 49)

To a solution of 1,6-di-O-benzyl-2,5-di-O-4-cyanobenzyl-D-mannitol, obtained as in example 4, (126 gm, 0.2 mmol) in formic acid (2 mL) was added Raney nickel. The suspension was heated at 60–80° C. for 1 hour. The reaction mixture was then filtered on Celite and the filtrate was concentrated in vacuo. The crude mixture was diluted with a solution of sodium bicarbonate and extracted with EtOAc and then methylene chloride. The combined organic layers was dried over sodium sulfate and concentrated in vacuo. Purification by flash chromatography eluting with 30% EtOAc in hexane afforded 50 mg (42%) of the title compound.

NMR (CDCl$_3$): 3.02 (d, J=5.5, 1H), 3.70 (m, 1H), 3.79 (m, 2H), 4.00 (t, J=5.9, 1H), 4.55 (s, 2H), 4.68 (d, J=12.1, 1H), 4.79 (d, J=12.3, 1H), 7.29 (m, 5H), 7.46 (d, J=8.1, 2H), 7.81 (d, J=9.0, 2H), 9.98 (s, 1H).

Example 48
Preparation of 1,6-di-O-(4-methylbenzyl)-2,5-di-O-benzyl-D-mannitol (compound no. 26)

The alkylation of 3,4-O-isopropylidene-D-mannitol with 4-methylbenzylbromide was carried out as described in example 2. The resulting 1,6-di-O-(4-methylbenzyl)-3,4-O-isopropylidene-D-mannitol was not characterized but reacted according to the conditions described in example 4. Purification by flash chromatography provided 60% yield of the title compound.

NMR (CDCl$_3$): 2.30 (s, 3H), 3.05 (s, 1H), 3.60 (m, 1H), 3.70 (m, 2H), 3.92 (s, 1H), 4.52 (s, 2H), 4.56 (d, J=11.0, 1H), 4.70 (d, J=11.0, 1H), 7.11 (d, J=7.5, 2H), 7.19 (d, J=7.5, 2H), 7.30 (s, 5H).

Example 49
Preparation of 1,6-di-O-(4-trifluoromethylbenzyl)-2,5-di-O-benzyl-D-mannitol (compound no. 27)

The alkylation of 3,4-O-isopropylidene-D-mannitol with 4-trifluoromethylbenzyl bromide was carried out as described in example 2. The resulting 1,6-di-O-(4-trifluoromethylbenzyl)-3,4-O-isopropylidene-D-mannitol was not characterized but reacted with benzyl bromide according to the conditions described in example 4. Purification by flash chromatography provided a 55% yield of the title compound.

NMR (CDCl$_3$): 3.48 (s, 1H), 3.68 (dd, J=5.5, 11.0, 1H), 3.75 (m, 2H), 4.00 (d, J=7.0, 1H), 4.60 (s, 2H), 4.61 (d, J=9.0, 1H), 4.72 (d, J=10.0, 1H), 7.30 (s, 5H), 7.41 (d, J=7.5, 2H), 7.55 (d, J=8.0, 2H).

Example 50
Preparation of 1,6-di-O-(4-cyanobenzyl)-2,5-di-O-benzyl-D-mannitol (compound no. 28)

The alkylation of 3,4-O-isopropylidene-D-mannitol with 4-trifluoromethylbenzyl bromide was carried out as described in example 2. The resulting 1,6-di-O-(4-trifluoromethylbenzyl)- 3,4-O-isopropylidene-D-mannitol was not characterized but reacted with benzyl bromide according to the conditions described in example 4. Purification by flash chromatography provided a 55% yield of the title compound.

NMR (CDCl$_3$): 2.90 (d, J=5.5, 1H), 3.70 (dd, J=5.0, 10.5, 1H), 3.75 (d, J=3.5, 2H), 3.79 (m, 2H), 3.98 (t, J=5.5, 1H), 4.58 (s, 2H), 4.60 (d, J=8, 1H), 4.73 (d, J=11.0, 1H), 7.30 (s, 5H), 7.39 (d, 7.5, 2H), 7.57 (d, J=7.5, 2H).

Example 51
Preparation of 1,6-di-O-(4-carbomethoxybenzyl)-2,5-di-O-benzyl-D-mannitol (compound no. 29)

The alkylation of 3,4-O-isopropylidene-D-mannitol with 4-carbomethoxybenzyl bromide was carried out as described in example 2. The resulting 1,6-di-O-(4-carbomethoxybenzyl)-3,4-O-isopropylidene-D-mannitol was not characterized but reacted with benzyl bromide according to the conditions described in example 4. Purification by flash chromatography provided a 42% yield.

NMR (CDCl$_3$): 2.98 (d, J=5.6, 1H), 3.69 (dd, J=10.5, 5.1, 1H), 3.77 (m, 2H), 3.90 (s, 3H), 3.98 (t, J=5.7, 1H), 4.58 (s, 2H), 4.62 (d, J=11.9, 1H), 4.73 (d, J=12.5, 1H), 7.30 (s, 5H), 7.37 (8.3, 2H), 7.98 (d, J=8.6).

Example 52
Preparation of 1,6-di-O-(4-fluorobenzyl)-2,5-di-O-benzyl-D-mannitol (compound no. 31)

The alkylation of 3,4-O-isopropylidene-D-mannitol with 4-fluorobenzyl bromide was carried out as described in example 2. The resulting 1,6-di-O-(4-fluorobenzyl)-3,4-O-isopropylidene-D-mannitol was not characterized but reacted with benzyl bromide according to the conditions described in example 4. Purification by flash chromatography provided a 52% yield.

NMR (CDCl$_3$): 3.00 (d,;J=5.5, 1H), 3.64 (dd, J=9.2, 5.4, 1H), 3.72 (m, 2H), 3.95 (t, J=5.7, 1H), 4.49 (s, 2H), 4.58 (d, J=11.1, 1H), 4.70 (d, J=11.2, 1H), 6.98 (t, J=7.8, 2H), 7.30 (m, 7H).

Example 53
Preparation of 1,6-di-O-(2-fluorobenzyl)-2,5-di-O-benzyl-D-mannitol (compound no. 32)

The alkylation of 3,4-O-isopropylidene-D-mannitol with 2-fluorobenzyl bromide was carried out as described in example 2. The resulting 1,6-di-O-(2-fluorobenzyl)-3,4-O-isopropylidene-D-mannitol was not characterized but reacted with benzyl bromide according to the conditions described in example 4. Purification by flash chromatography provided a 66% yield.

NMR (CDCl$_3$): 1.2 (d, J=7.4, 1H), 3.63 (m, 1H), 3.70 (m, 2H), 3.87 (d, J=5.7, 1H), 4.50 (s, 2H), 4.54 (d, J=12.1, 1H), 4.65 (d, J=11.1, 1H), 6.95 (t, J=9.1, 1H), 7.02 (t, J=7.5, 1H), 7.23, m, 6H), 7.31 (t, J=7.4, 1H).

Example 54
Preparation of 1,6-di-O-(2,4-fluorobenzyl)-2,5-di-O-benzyl-D-mannitol (compound no. 33)

The alkylation of 3,4-O-isopropylidene-D-mannitol with 2,4-difluorobenzyl bromide was carried out as described in example 2. The resulting 1,6-di-O-(2,4-difluorobenzyl)-3,4-O-isopropylidene-D-mannitol was not characterized but reacted with benzyl bromide according to the conditions described in example 4. Purification by flash chromatography provided a 49% yield.

NMR (CDCl$_3$): 3.00 (d, J=5.5, 1H), 3.68 (dd, J=11.3, 5.9, 1H), 3.72 (m, 2H), 3.95 (t, J=6.4, 1H), 4.49 (s, 2H), 4.56 (d, J=11.6, 1H), 4.70 (d, J=11.2, 1H), 6.81 (t, J=5.3, 2H), 7.30 (m, 7H).

Example 55
Preparation of 1,6-di-O-(2-fluorobenzyl)-2,5-di-O-(4-bromobenzyl)-D-mannitol (compound no. 34)

The alkylation of 3,4-O-isopropylidene-D-mannitol with 2-fluorobenzylbromide was carried out as described in example 2 by substituting benzylbromide with 2-fluorobenzylbromide. The resulting 1,6-di-O-(2-fluorobenzyl)-3,4-O-isopropylidene-D-mannitol was not characterized but reacted with 4-bromobenzyl bromide using the conditions described in example 4. Purification by flash chromatography provided 60% yield of the title compound, mp. 107° C.

NMR (CDCl$_3$): 3.00 (d, J=5.81H), 3.68–3.70 (m, 1H), 3.77–3.93 (m, 2H), 3.92 (d, J=5.8, 1H), 4.53 (d, J=11.7, 1H), 4.62 (d, J=11.7, 1H), 4.60 (s, 2H), 7.00–7.42 (m, 8H).

Example 56
Preparation of 1,6-di-O-(2-fluorobenzyl)-2,5-di-O-(4-methoxybenzyl)-D-mannitol (compound no. 36)

The alkylation of 3,4-O-isopropylidene-D-mannitol with 2-fluorobenzylbromide was carried out as described in example 2 by substituting benzylbromide with 2-fluorobenzylbromide. The resulting 1,6-di-O-(2-fluorobenzyl)-3,4-O-isopropylidene-D-mannitol was not characterized but reacted with 4-methoxybenzyl bromide in the conditions described in example 4. Purification by flash chromatography provided 72% yield of the title compound.

NMR (CDCl$_3$): 3.00 (d, J=5.5, 1H), 3.67 (m, 1H), 3.73 (m, 1H), 3.78 (s, 3H), 3.92 (t, J=5.5, 1H), 4.50 (d, J=11.0, 1H), 4.60 (s, 2H), 4.66 (d, J=11.0, 1H), 6.83 (d, J=9.0, 2H), 7.03 (t, J=9.0, 1H), 7.10 (t, J=7.5, 1H), 7.22 (d, J=7.5, 2H), 7.27 (m, 1H), 7.39 (t, J=7.5, 1H).

Example 57
Preparation of 1,6-di-O-(2-fluorobenzyl,-2,5-di-O-(4-methylthiobenzyl)-D-mannitol (compound no. 68)

The alkylation of 3,4-O-isopropylidene-D-mannitol with 2-fluorobenzyl bromide was carried out as described in example 2. The resulting 1,6-di-O-(2-fluorobenzyl)-3,4-O-isopropylidene-D-mannitol was not characterized but reacted with 4-methylthiobenzyl bromide according to the conditions described in example 4. Purification by flash chromatography provided a 15% yield.

NMR (CDCl$_3$): 2.45 (s, 3H), 3.00 (d, J=5.3, 1H), 3.69–3.78 (m, 3H), 3.93 (s, 1), 4.54 (d, J=11.5, 1H), 4.61 (d, J=3.0, 2H), 4.67 (d, J=11.5, 1H), 7.03 (t, J=7.5, 1H), 7.10 (t, J=7.5, 1H), 7.18–7.29 (m, 5H), 7.38 (t, J=7.0, 1H).

Example 58
Preparation of 1,6-di-O-(4-benzyloxybenzyl)-2,5-di-O-(4-fluorobenzyl)-D-mannitol (compound no. 58)

The alkylation of 3,4-O-isopropylidene-D-mannitol with 4-benzyloxybenzyl chloride was carried out as described in example 2 by substituting benzylbromide with 4-benzyoxybenzylchloride. The resulting 1,6-di-O-(4-benzyloxybenzyl)-3,4-O-isopropylidene-D-mannitol was not characterized but reacted with 4-fluorobenzyl bromide in the conditions described in example 4.

NMR (CDCl$_3$): 3.04 (d, J=5.5, 1H), 3.62 (dd, J=3.5, 9.0, 1H), 3.69 (d, J=3.5, 1H), 3.71 (m, 3H), 3.92 (t, J=6.0, 1H), 4.46 (s, 2H), 4.53 (d, J=11.0, 1H), $0.64 (d, J=11.0, 1H), 5.04 (s, 1H), 6.90–7.00 (m, 4H), 7.21–7.27 (m, 4H), 7.31 (t, J=7.5, 1H), 7.37 (t, J=7.5, 2H), 7.41 (d, J=7.5, 2H).

Example 59
Preparation of 1,6-di-O-(2-methylbenzyl)-2,5-di-O-(4-fluorobenzyl)-D-mannitol (compound no. 37)

The alkylation of 3,4-O-isopropylidene-D-mannitol with 2-methylbenzyl chloride was carried out as described in example 2 by substituting benzyl bromide with 2-methylbenzyl chloride. The resulting 1,6-di-O-(2-methylbenzyl)-3,4-O-isopropylidene-D-mannitol was not characterized but reacted with 4-fluorobenzyl bromide in the conditions described in example 4. Purification by flash chromatography provided 71% yield of the title compound.

NMR (CDCl$_3$): 2.30 (s, 3H), 3.02 (d, J=5.5, 1H), 3.65 (m, 1H), 3.73 (m, 2H), 3.93 (t, J=5.5, 1H), 4.53 (s, 2H), 4.55 (d, J=11, 1H), 4.70 (d, J=11, 1H), 6.90–7.30 (m, 8H).

Example 60
Preparation of 1,6-di-O-(2-fluorobenzyl)-2,5-di-O-(2-methylbenzyl)-D-mannitol (compound no. 38)

The alkylation of 3,4-O-isopropylidene-D-mannitol with 2-fluorobenzyl bromide was carried out as described in example 2 by substituting benzyl bromide with 2-fluorobenzyl bromide. The resulting 1,6-di-O-(2-fluorobenzyl)-3,4-O-isopropylidene-D-mannitol was not characterized but reacted with 2-methylbenzyl bromide in the conditions described in example 4. Purification by flash chromatography provided 61% yield of the title compound.

NMR (CDCl$_3$): 2.30 (s, 3H), 2.96 (d, J=6.5, 1H), 3.69 (dd, J=4.5, 8.5, 1H), 3.77 (m, 2H), 3.92 (t, J=6.0, 1H), 4.53 (d, J=11.5, 1H), 4.60 (s, 2H), 4.73 (d, J=11.0, 1H), 7.03 (t, J=8, 1H), 7.06–7.25 (m, 6H), 7.38 (t, J=8, 1H).

Example 61
Preparation of 1,6-di-O-(2-fluorobenzyl)-2,5-di-O-(4-methylbenzyl)-D-mannitol (compound no. 56)

The alkylation of 3,4-O-isopropylidene-D-mannitol with 2-fluorobenzyl bromide was carried out as described in example 2 by substituting benzyl bromide with 2-fluorobenzyl bromide. The resulting 1,6-di-O-(2-fluorobenzyl)-3,4-O-isopropylidene-D-mannitol was not characterized but reacted with 4-methylbenzyl bromide in the conditions described in example 4. Purification by flash chromatography provided 61% yield of the title compound.

NMR (CDCl$_3$): 2.33 (s, 3H), 3.00 (d, J=5.5, 1H), 3.63 (dd, J=4.0, 9.5, 1H), 3.72 (m, 2H), 3.77 (d, J=4.0, 1H), 3.92 (t, J=4.0, 1H), 4.53 (d, J=11.0, 1H), 4.58 (d, 2H), 4.68 (d, J=11.5, 1H), 7.02 (t, J=9.0, 1H), 7.10 (m, 3H), 7.19 (d, J=7.5, 2H), 7.25 (dd, J=7.5, 7.0, 1H), 7.39 (t, J=7.5, 1H).

Example 62
Preparation of 1,6-di-O-(2,6-difluorobenzyl)-2,5-di-O-(4-fluorobenzyl)-D-mannitol (compound no. 39)

The alkylation of 3,4-O-isopropylidene-D-mannitol with 2,6-difluorobenzyl chloride was carried out as described in example 2 by substituting benzyl bromide with 2,6-difluorobenzylchloride. The resulting 1,6-di-O-(2,6-difluorobenzyl)-3,4-O-isopropylidene-D-mannitol was not characterized but reacted with 4-fluorobenzyl bromide using the conditions described in example 4. Purification by flash chromatography provided 68% yield of the title compound, mp. 110° C.

NMR (CDCl$_3$): 2.92 (d, J=7.0, 1H), 3.65–3.71 (m, 2H), 3.70 (dd, J=9.5, 3.5, 1H), 3.85 (t, J=6.5, 1H), 4.53 (d, J=11.0, 1H), 4.61 (d, J=11.0, 1H), 4.63 (s, 2H), 6.89 (t, J=8.0, 2H), 6.97 (t, J=9.0, 2H), 7.26 (m, 3H).

Example 63
Preparation of 1,6-di-O-(2-fluorobenzyl)-2,5-di-O-(4-fluorobenzyl)-D-mannitol (compound no. 40)

The alkylation of 3,4-O-isopropylidene-D-mannitol with 2-fluorobenzyl bromide was carried out as described in example 2 by substituting benzyl bromide with 2-fluorobenzyl bromide. The resulting 1,6-di-O-(2-fluorobenzyl)-3,4-O-isopropylidene-D-mannitol was not characterized but reacted with 4-fluorobenzyl bromide in the conditions described in example 6 substituting the 4-cyanobenzylbromide with 4-fluorobenzyl bromide. Purification by flash chromatography provided 60% yield of the title compound, mp. 71° C.

NMR (CDCl$_3$): 3.00 (s, 1H), 3.68 (m, 1H), 3.78 (m, 2H), 3.92 (s, 1H), 4.54 (d, J=11.3, 1H), 4.60 (s, 2H), 4.67 (d, J=11.4, 1H), 6.97 (m, 2H), 7.03 (t, J=9.2, 1H), 7.09 (t, J=7.5, 1H), 7.26 (m, 2H), 7.37 (t, J=7.4, 1H).

Example 64
Preparation of 1,6-di-O-(4-bromobenzyl)-2,5-di-O-benzyl-D-mannitol (compound no. 54)

The alkylation of 3,4-O-isopropylidene-D-mannitol with 2-fluorobenzyl bromide was carried out as described in example 2 by substituting benzyl bromide with 4-bromobenzyl bromide. The resulting 1,6-di-O-(4-bromobenzyl)-3,4-O-isopropylidene-D-mannitol was not characterized but reacted with 4-fluorobenzyl bromide in the conditions described in example 4 substituting the 4-cyanobenzylbromide with benzyl bromide. Purification by flash chromatography provided 56% yield of the title compound.

NMR (CDCl$_3$): 3.00 (br, 1H), 3.67 (dd, J=5.5, 11.0, 1H), 3.73 (d, J=3.5, 1H), 3.72 (m, 2H), 3.97 (d, J=5.5, 1H), 4.50 (s, 2H), 4.60 (d, J=11.5, 1H), 4.73 (d, J=11.5, 1H), 7.19 (d, J=7.5. 2H), 7.32 (s, 5H), 7.45 (d, J=7.0, 2H).

Example 65
Preparation of 1,6-di-O-(4-chlorobenzyl)-2,5-di-O-benzyl-D-mannitol (compound no. 55)

The alkylation of 3,4-O-isopropylidene-D-mannitol with 4-chlorobenzyl chloride was carried out as described in example 2 by substituting benzyl bromide with 4-chlorobenzyl chloride. The resulting 1,6-di-O-(4- chlorobenzyl)-3,4-O-isopropylidene-D-mannitol was not characterized but reacted with 4-chlorobenzyl bromide in the conditions described in example 4 substituting the 4-cyanobenzylbromide with benzyl bromide. Purification by flash chromatography provided 62% yield of the title compound.

NMR (CDCl$_3$): 2.97 (br, 1H), 3.65 (dd, J=5.5, 11.0, 1H), 3.70 (d, J=3.5, 1H), 3.72 (m, 2H), 3.95 (d, J=5.5, 1H), 4.49 (s, 2H), 4.58 (d, J=12.0, 1H), 4.71 (d, J=12.0, 1H), 7.30 (m, 9H).

Example 66
Preparation of 1,6-di-O-(4-carboxybenzyl)-2,5-di-O-benzyl-D-mannitol (compound no. 51)

The base hydrolysis of 1,6-di-O-(4-cyanobenzyl)-2,5-di-O-benzyl-D-mannitol prepared in example 50 was carried out as in example 45, affording the title compound in 41% yield.

NMR (CDCl$_3$): 3.70 (m, 3H), 3.90 (s, 2H), 4.00 (d, J=5.5, 1H), 4.58 (s, 3H), 4.71 (d, J=11.2, 1H), 7.30 (m, 7H), 8.02 (d, J=7.6, 2H),

Example 67
Preparation of 1,6-di-O-cyclopropylmethyl-2,5-di-O-dibenzyl-D-mannitol (compound no. 89)

The alkylation of 3,4-O-isopropylidene-D-mannitol with cyclopropylmethyl bromide was carried out as described in example 2 by substituting benzyl bromide with cyclopropylmethyl bromide. The resulting 1,6-di-O-cyclopropyhnethyl-3,4-O-isopropylidene-D-mannitol was not characterized but reacted with benzyl bromide in the conditions described in example 4. Purification by flash chromatography provided a 38% yield of the title compound.

NMR (CDCl$_3$): 0.19 (d, J=4.8, 2H), 0.52 (d, J=7.5, 2H), 1.04 (m, 1H), 3.22 (d, J=5.8, 1H), 3.31 (t, J=5.1, 2H), 3.65 (m, 1H), 3.74 (m, 2H), 3.94 (t, J=5.6, 1H), 4.63 (d, J=11.4, 1H), 4.74 (d, J=11.6, 1H), 7.30 (s, 5H).

Example 68
Preparation of 1,6-di-O-allyl-2,5-di-O-benzyl-D-mannitol (compound no. 90)

The alkylation of 3,4-O-isopropylidene-D-mannitol with allyl bromide was carried out as described in example 2 by substituting benzyl bromide with allyl bromide. The resulting 1,6-di-O-cyclopropylmethyl-3,4-O-isopropylidene-D-mannitol was not characterized but reacted with benzyl bromide in the conditions described in example 4. Purification by flash chromatography provided a 50% yield of the title compound.

NMR (CDCl$_3$): 3.06 (d, J=6.0, 1H), 3.63 (dd, J=9.6, 4.8, 5, 1H), 3.72 (m, 2H), 3.93 (t, J=5.7, 1H), 4.01 (d, J=5.4, 2H), 4.60 (d, J=11.3, 1H), 4.74 (d, J=11.4, 1H), 5.17 (d, J=10.5, 1H), 5.27 (d, J=17.4, 1H), 5.90 (m, 1H), 7.30 (s, 5H).

Example 69
Preparation of 1,6-di-O-(4-hydroxybenzyl)-2,5-di-O-(4-fluorobenzyl)-D-mannitol (compound no. 4)

Following the indications of step B of example 8, the product from example 58 was hydrogenlyzed to the title compound (37%) and to a smaller yield (12%) of 1-O-(4-hydroxybenzyl)-6-O-(4-benzyloxybenzyl)-2,5-di-O-(4-fluorobenzyl)-D-mannitol.

1-O-(4-hydroxybenzyl)-6-O-(4-benzyloxybenzyl)-2,5-di-O-(4-fluorobenzyl)-D-mannitol (compound no. 76)

NMR (CDCl$_3$): 3.23 (d, J=5.5, 1H), 3.26 (d, J=5.5, 1H), 3.64–3.67 (m, 2H), 3.68–3.76 (m, 4H), 3.96–3.98 (m, 2H), 4.45 (s, 2H), 4.48 (s, 2H), 4.54 (d, J=11.5, 2H), 4.66 (d, J=11.5, 2H), 6.73 (d, J=7.0, 2H), 6.90–7.00 (m, 6H), 7.10 (d, J=8.8, 2H), 7.20–7.45 (m, 11H).

1,6-di-O-(4-hydroxybenzyl)-2,5-di-O-(4-fluorobenzyl)-D-mannitol

NMR (CDCl$_3$): 3.34 (d, J=5.5, 1H), 3.62 (m, 1H), 3.72 (m, 2H), 3.92 (t, J=5.5, 1H), 4.46 (s, 2H), 4.52 (d, J=11.0, 1H), 4.63 (d, J=11.0, 1H), 5.04 (s, 2H), 6.92–7.00 (m, 4H), 7.2–7.50 (m, 9H).

Example 70
Preparation of 1,2,6-tri-O-benzyl-5-O-(4-fluorobenzyl)-D-mannitol (compound no. 8)

Step A. 1,6-di-O-benzyl-2-O-(4-fluorobenzyl)-3,4-isopropylidene-D-mannitol

To a solution of 1,6-di-O-benzyl-3,4-O-isopropylidene-D-mannitol (402 mg, 1 mmol), obtained as in example 2, in toluene (10 mL) was added silver oxide (348 mg, 1.5 mmol) and 4-fluorobenzyl bromide (1.2 g, 0.63 mmol). The mixture was stirred at room temperature for 15 h. The mixture was then filtered and the filtrate was concentrated to dryness to afford the crude product that was purified by flash chromatography eluting with 70% EtOAc in hexane.

NMR (CDCl$_3$): 1.33 (s, 3H), 1.35 (s, 3H), 3.10 (d, J=3.5, 1H), 3.55 (dd, J=9.5, 5.5, 1H), 3.62–3.82 (m, 3H), 3.69–3.72 (m, 1H), 3.82 (d, J=12.0, 1H), 3.96 (t, J=7.5, 1H), 4.09 (t, J=7.5, 1H), 4.54 (s, 2H), 4.55 (s, 2H), 4.60 (d, J=12.0, 1H), 4.75 (d, J=12.0, 1H), 6.94 (dd, J=9.5, 7.0, 2H), 7.27 (dd, J=8.5, 6.0, 2H), 7.30–7.34 (m, 10H).

Step B. 1,2,6-tri-O-benzyl-5-O-(4-fluorobenzyl)-D-mannitol

The product thus purified was then subjected to a further alkylation with benzyl bromide under conditions described in example 2 to provide the title compound in a 71% yield.

NMR (CDCl$_3$): 3.00 (d, J=5.5, 2H), 3.65 (m, 2H), 3.75 (m, 4H), 3.96 (dd, J=6.5, 11.5, 2H), 4.49 (s, 2H), 4.53 (s, 2H), 4.58 (d, J=10.5, 2H), 4.70 (d, J=11.5, 1H), 4.72 (d, J=11.5, 1H), 6.90 (t, J=7, 2H), 7.30 (17H).

Example 71
Preparation of 1,2,6-tri-O-benzyl-D-mannitol (compound no. 98)

Following the indications outlined in step A of example 70 but substituting 4-fluorobenzyl bromide with benzyl bromide, the title compound was obtained in 89% yield.

NMR (CDCl$_3$): 2.40 (dd, J=7.5, 4, 1H), 3.00 (d, J=7.5, 1H), 3.07 (d, J=4, 1H), 3.58 (m, 1H), 3.68 (m, 2H), 3.80 (m, 3H), 3.94 (dd, J=13, 7, 1H), 4.54 (s, 2H), 4.57 (d, J=12.0, 1H), 4.59 (d, J=11.0, 1H), 4.62 (d, J=11.0, 1H), 4.72 (d, J=11.0, 1H), 7.32 (m, 15H).

Example 72
Preparation of 1,2,6-tri-O-benzyl-5-O-(4-aminobenzyl)-D-mannitol (compound no. 9)

A solution of 1,2,6-tri-O-benzyl-5-O-(4-nitrobenzyl)-D-mannitol (59 mg, 0.1 mmol), obtained as in example 103 in MeOH (5 mL) was hydrogenated at atmospheric pressure using 5% Pd/C for 1 h. The catalyst was removed by filtration and the filtrate was evaporated to dryness to afford 75% of the title compound.

NMR (CDCl$_3$): 3.00 (d, J=5.5, 1H), 3.65 (m, 2H), 3.75 (m, 4H), 3.96 (t, J=6.0, 2H), 4.49 (s, 2H), 4.53 (s, 2H), 4.58 (d, J=11.0, 2H), 4.70 (d, J=11.4, 1H), 4.73 (d, J=11.2, 1H), 7.00 (m, 2H), 7.30 (m, 17H).

Example 73
Preparation of 1,2,5-tri-O-benzyl-6-O-(2-fluorobenzyl)-D-mannitol (compound no. 10)

Alkylation of 1,2,6-tri-O-benzyl-3,4-O-isopropylidene-D-mannitol obtained as in example with 2-fluorobenzylbromide was conducted as described in example 4 using 2-fluorobenzylbromide instead of benzyl bromide. After treatment with methanolic HCl, the title compound was obtained in 89% yield.

NMR (CDCl$_3$): 3.03 (t, J=8.5, 2H), 3.65–3.79 (m, 6H), 3.96 (d, J=11.0, 2H), 4.54 (s, 2H), 4.62 (m, 4H), 4.71 (d, J=12.5, 1H), 4.73 (d, J=12.5, 1H), 7.02 (t, J=9.5, 1H), 7.09 (t, J=7.5, 1H), 7.30 (m, 16H), 7.39 (t, J=7.5, 1H).

Example 74
Preparation of 1,6-di-O-benzy-2-O-(4-nitrobenzl)-D-mannitol (compound no. 99) and of 1,6-di-O-benzyl-2,5-di-O-(4-nitrobenzyl)-D-mannitol (compound no.13)

To a solution of 1,6-di-O-benzyl-3,4-O-isopropylidene-D-mannitol, obtained as in example 2, (402 mg, 1 mmol) in toluene (10 mL) was added freshly prepared silver oxide (464 mg, 2 mmol) and 4-nitrobenzylbromide (648 mg, 3 mmol). The suspension was stirred at room temperature overnight. More silver oxide (464 mg, 2 mmol) was added and the reaction was refluxed for 24 h. The insoluble material was filtered off and the filtrate was concentrated in vacuo. The residue was purified by chromatography on silica gel eluting with 50% EtOAc in hexane to yield 60% of 1,6-di-O-benzyl-2-O-(4-nitrobenzyl)-D-mannitol and 12% of 1,6-di-O-benzyl-2,5-di-O-(4-nitrobenzyl)-D-mannitol.

1,6-di-O-benzyl-2-O-(4-nitrobenzyl)-D-mannitol

NMR (CDCl$_3$): 3.14 (d, J=7.0, 1H0, 3.20 (d, J=7.0, 1H), 3.49 (d, J=6.0, 1H), 3.60 (dd, J=5.5, 9.0, 1H), 3.69 (m, 2H), 3.77 (m, 2H), 3.82 (t, J=7.0, 1H), 3.90 (m, 1H), 4.02 (t, J=6.0, 1H), 4.09 (d, J=7.0, 1H), 4.11 (d, J=7.0, 1H), 7.35 (m, 10H), 7.40 (d, J=8.0, 1H), 8.10 (d, J=8.0, 1H).

1,6-di-O-benzyl-2,5-di-O-(4-nitrobenzyl)-D-mannitol

NMR (CDCl$_3$): 3.04 (d, J=5.5, 1H), 3.70 (m, 1H), 3.78 (m, 1H), 4.00 (t, J=5.5, 1H), 4.53 (s, 2H), 4.70 (d, J=1.0, 1H), 4.82 (d, J=11.0, 1H), 7.30 (m, 5H), 7.43 (d, J=8.5, 2H), 8.14 (d, J=8.5, 2H).

Example 75
Preparation of 1,6-di-(4-hydroxymethylbenzyl)-2,5-dibenzyl-D-mannitol (compound no. 48)

In a similar fashion as described in example 43, 2,5-di-O-benzyl-1,6-di-O-(4-carbomethoxybenzyl)-D-mannitol was reduced to the desired product with lithium aluminium hydride in 83% yield.

NMR (CDCl$_3$): 3.02 (d, J=6.6, 1H), 3.65 (dd, J=3.6, 9.2, 1H), 3.74 (m, 3H), 3.96 (t, J=5.5, 1H), 4.53 (s, 2H), 4.60 (d, J=11.5, 1H), 4.66 (s, 2H), 4.71 (d, J=12.0, 1H), 7.30 (m, 9H).

Example 76
Preparation of 1,6-di-O-benzyl-2,5-di-O-(3-hydroxybenzyl)-D-mannitol (compound no. 3)

As described in the example 4, the title compound was prepared by reacting 1,6-di-O-benzyl-3,4-isopropylidene-D-mannitol with 3-benzyloxybenzyl bromide. After purification by flash chromatography, the title compound was obtained in 83% yield.

NMR (CDCl$_3$): 3.30 (d, J=5.5, 1H), 3.69 (dd, J=11.0, 5.5, 1H), 3.75 (m, 2H), 4.45 (d, J=11.0, 1H), 4.53 (s, 2H), 4.65 (d, J=11.0, 1H), 6.19 (s, 1H), 6.70–7.30 (m, 9H).

Example 77
Preparation of 1,6-di-(2-fluorobenzyl)-2,5-di-(4-benzyloxybenzyl)-D-mannitol (compound no. 7)

As described in the example 4, substituting 1,6-di-O-benzyl-3,4-O-isopropylidene-D-mannitol with 1,6-di-O-(2-fluorobenzyl)-3,4-O-isopropylidene-D-mannitol, the title compound was obtained in 51% yield.

NMR (CDCl$_3$): 3.00 (d, J=6.0, 1H), 3.67 (dd, J=5.5, 9.5, 1H), 3.76 (m, 2H), 3.92 (t, J=5.5, 1H), 4.51 (d, J=11.0, 1H), 4.60 (d, J=3.5, 2H), 4.63 (d, J=12.0, 1H), 5.04 (s, 2H), 6.89 (d, J=7.5, 2H), 7.01 (t, J=9.0, 1H), 7.08 (t, J=7.5, 1H), 7.22 (d, J=7.5, 2H), 7.28–7.41 (m, 7H).

Example 78
Preparation of 1,6-di-(2-fluorobenzyl)-2,5-di-(4-hydroxybenzyl)-D-mannitol (compound no. 5)

As described in the example 16 and substituting 1,6-di-O-benzyl-2,5-di-O-(4-benzyloxybenzyl)-D-mannitol with 1,6-di-O-(2-fluorobenzyl)-2,5-di-O-(4-benzyloxybenzyl)-D-mannitol, careful hydrogenation afforded the title compound in 85% yield.

NMR (CDCl$_3$): 3.41 (d, J=5.5, 1H), 3.67 (dd, J=11.0, 6.0, 1H), 3.74 (d, J=8.0, 2H), 3.98 (t, J=5.5, 1H), 4.42 (d, J=11.0, 1H), 4.59 (s, 2H), 4.61 (d, J=11.0, 1H), 6.31 (s, 1H), 6.62 (d, J=9.5, 2H), 7.00–7.40 (m, 6H).

Example 79
Preparation of 1,6-di-O-(4-fluorobenzyl)-2,5-di-O-(3,4-dihydroxybenzyl)-D-mannitol (compound no. 69)

Step A. 1,6-di-O-(4-fluorobenzyl)-2,5-di-O-(3,4-dibenzyloxybenzyl)-D-mannitol (compound no 75)

The alkylation of 3,4-O-isopropylidene-D-marmitol with 4-fluoromethylbenzylbromide was carried out as described in example 2. The resulting 1,6-di-O-(4-fluoromethylbenzyl)-3,4-O-isopropylidene-D-mannitol was not characterized but reacted with 3,4-dibenzyloxybenzyl chloride according to the conditions described in example 4. Purification by flash chromatography provided a 8% yield of the title compound.

NMR (CDCl$_3$): 3.02 (s, 2H), 3.62–3.59 (m, 2H), 3.67–3.74 (m, 4H), 3.92 (d, J=6.5, 2H), 4.44 (s, 4H), 4.53 (d, J=11.5, 2H), 4.65 (d, J=11.5, 2H), 5.11 (s, 2H), 5.15 (s, 2H), 6.82 (d, J=8.0, 2H), 6.89 (d, J=9.0, 2H), 6.95–6.99 (m, 6H), 7.24–7.38 (m, 17H), 7.42–7.45 (m, 7H).

Step B. 1,6-di-O-(4-fluorobenzyl)-2,5-di-O-(3,4-dihydroxybenzyl)-D-mannitol

Hydrogenolysis of the product of step A of this example according to the conditions of step B of the example 8, the title compound was obtained in 47% yield.

NMR (CDCl$_3$): 3.00 (s, 2H), 3.59 (t, J=5.5, 2H), 3.66 (m, 6H), 4.25 (d, J=11.5, 2H), 4.42 (d, J=11.0, 2H), 6.54 (d, J=8.0, 2H), 6.61 (d, J=8.0, 2H), 6.72 (s, 2H), 6.76 (s, 2H), 6.93 (t, J=7.5, 6H), 7.19 (t, J=6.5, 4H).

Example 80
Preparation of 1,6-di-O-(4-fluorobenzyl)-2,5-O-(3,5-dihydroxybenzyl)-D-mannitol (compound no. 70)

Step A. 1,6-di-O-(4-fluorobenzyl)-2,5-O-(3,5-dibenzyloxybenzyl)-D-mannitol (compound no. 73)

The alkylation of 3,4-O-isopropylidene-D-mannitol with 4-fluorobenzyl bromide was carried out as described in example 2. The resulting 1,6-di-O-(4-fluorobenzyl)-3,4-O-isopropylidene-D-mannitol was not characterized but reacted with 3,5-dibenzyloxybenzyl chloride according to the conditions described in example 4. Purification by flash chromatography provided a 26% yield of the title compound.

NMR (CDCl$_3$): 2.98 (s, 1H), 3.68–3.78 (m, 3H), 3.95 (s, 1H), 4.54–4.66 (m, 4H), 4.97 (s, 4H), 6.52–6.58 (m, 3H), 6.97–7.07 (m, 2H), 7.20–7.38 (m, 12H).

Step B. 1,6-di-O-(4-fluorobenzyl)-2,5-O-(3,5-dihydroxybenzyl)-D-mannitol

Hydrogenolysis of the product of step A of this example according to the conditions of step B of the example 8, the title compound was obtained in 83% yield.

NMR (CDCl$_3$) δ: 3.63–3.68 (m, 4H), 3.76 (bs, 2H), 3.86 (d, 10, 2H), 3.91 (t, J=6.0, 2H), 4.42 (s, 4H), 4.48 (d, J=11.4, 2H), 4.68 (d, J=11.9, 2H), 6.25 (s, 4H), 6.38 (s, 8H), 8.13 (s, 8H).

Example 81
Preparation of 1,6-di-O-(4-tert-butyl-2,2-di-O-(4-fluorobenzyl)-D-mannitol (compound no. 42)

The alkylation of 3,4-O-isopropylidene-D-mannitol with 4-tert-butylbenzyl bromide was carried out as described in example 2. The resulting 1,6-di-O-(4-tert-buthylbenzyl)-3,4-O-isopropylidene-D-mannitol was not characterized but reacted with 4-fluorobenzyl bromide according to the conditions described in example 4. Purification by flash chromatography provided a 32% yield of the title compound.

NMR (CDCl$_3$): 1.31 (s, 18H), 3.05 (d, J=4.5, 2H), 3.73 (s, 2H), 3.75 (s, 2H), 3.94 (s, 2H), 4.51 (s, 4H), 4.55 (d, J=11.5, 2H), 4.67 (d, J=11.0, 2H), 6.97 (t, J=8, 4H), 7.25 (s, 8H), 7.35 (d, J=7.0, 4H).

Example 82
Preparation of 1,6-di-O-(2-thienylmethyl)-2,5-di-O-benzyl-L-mannitol (compound no. 92)

The alkylation of 3,4-O-isopropylidene-D-mannitol with 2-thienylmethyl bromide was carried out as described in example 2. The resulting 1,6-di-O-(2-thienylmethyl)-3,4-O-isopropylidene-D-mannitol was not characterized but reacted with benzyl bromide according to the conditions described in example 4. Purification by flash chromatography provided a 40% yield of the title compound.

NMR (CDCl$_3$): 2.95 (d, J=6.0, 1H), 3.65 (m, 1H), 3.71 (m, 2H), 3.92 (m, 1H), 4.56 (d, J=11.5, 1H), 4.68 (s, 2H), 4.71 (d, J=11.2, 1H), 6.95 (m, 2H), 7.25 (m, 1H), 7.30 (s, 5H).

Example 83
Preparation of 1,6-di-O-(2-thienylmethyl)-2,5-di-O-(4-fluorophenylmethyl)-D-mannitol (compound no. 93)

The alkylation of 3,4-O-isopropylidene-D-mannitol with 2-thienylmethyl bromide was carried out as described in example 2. The resulting 1,6-di-O-(2-thienylmethyl)-3,4-O-isopropylidene-D-mannitol was not characterized but reacted with 4-fluorobenzyl bromide according to the conditions described in example 4. Purification by flash chromatography provided a 42% yield of the title compound.

NMR (CDCl$_3$): 2.94 (d, J=3.1, 1H), 3.64 (m, 1H), 3.71 (m, 2H), 3.89 (s, 1H), 4.53 (d, J=11.2, 1H), 4.68 (d, J=11.2, 1H), 4.70 (s, 2H), 7.00 (m, 4H), 7.26 (m, 3H).

Example 84
Preparation of 1,6-di-O-cinnamyl-2,5-di-O-benzyl-D-mannitol (compound no. 94)

The alkylation of 3,4-O-isopropylidene-D-mannitol with cinnamyl bromide was carried out as described in example 2. The resulting 1,6-di-O-cinnamyl-3,4-O-isopropylidene-D-mannitol was not characterized but reacted with benzyl bromide according to the conditions described in example 4. Purification by flash chromatography provided a 37% yield of the title compound.

NMR (CDCl$_3$): 3.07 (d, J=6.0, 1H), 3.68 (dd, J=6.0, 11.0, 1H), 3.76 (m, 2H), 3.98 (t, J=5.5, 1H), 4.26 (dd, J=12.4, 5.8, 1H), 4.35 (dd, J=12.5,5.9, 1H), 4.56 (s, 2H), 6.27 (m, 1H), 6.58 (d, J=15.7, 1H), 7.21–7.36 (m, 10H).

Example 85
Preparation of 1,6-di-O-(3-phenyl-1-propyl)-2-O-(4-fluorobenzyl)-D-mannitol (compound no. 100)

Step A. 1,6-di-O-(3-phenyl-1-propyl)-3,4-O-isopropylidene-D-mannitol

The alkylation of 3,4-O-isopropylidene-D-mannitol with cinnamyl bromide was carried out as described in example 2. The resulting 1,6-di-O-cinnamyl-3,4-O-isopropylidene-D-mannitol was not characterized but hydrogenated using 5% palladium on charcoal in a methanolic solution at one atmosphere of hydrogen. Filtration and evaporation of the filtrate to dryness afforded the intermediate.

NMR (CDCl$_3$): 1.37 (s, 6H), 1.73 (q, J=7.0, 4H), 2.70 (t, J=7.5, 4H), 3.48–3.55 (m, 6H), 3.68–3.70 (m, 2H), 3.78 (s, 2H), 3.89–3.91 (m, 2H), 7.17–7.20 (m, 5H), 7.26–7.29 (m, 5H).

Step B. 1,6-di-O-(3-phenyl-1-propyl)-2,5-di-O-(4-fluorobenzyl)-3,4-O-isopropylidene-D-mannitol 1,6-Di-O-(3-phenyl-1-propyl)-3,4-O-isopropylidene-D-mannitol (90 mg, 0.20 mmol) was alkylated with 4-fluorobenzyl bromide as described in example 3. Purification by flash chromatography eluting with 30% EtOAc in hexane afforded the monoalkylated product (49%) and the dialkylated product (43%).

1,6-di-O-(3-phenyl-1-propyl)-2-O-(4-fluorobenzyl)-3,4-O-isopropylidene-D-mannitol NMR (CDCl$_3$): 1.36 (s, 6H), 1.91 (q, J=6.5, 4H), 2.68 (q, J=8.0, 4H), 3.60–3.78 (m, 6H), 3.95 (t, J=7.0, 1H), 4.08 (t, J=7.0, 1H), 4.66 (d, J=10.0, 1H), 4.79 (d, J=11.5, 1H), 7.00 (t, J=8.5, 2H), 7.17–7.18 (m, 6H), 7.25–7.28 (m, 4H), 7.33–7.34 (m, 2H).

1,6-di-O-(3-phenyl-1-propyl)-2,5-di-O-(4-fluorobenzyl)-3,4-O-ispropylidene-D-mannitol NMR (CDCl$_3$): 1.37 (s, 6H0, 1.87 (q, J=6.0, 4H), 2.66 (t, J=7.5, 4H), 3.40 (t, J=5.5, 4H), 3.52–3.55 (m, 2H), 3.66–3.69 (m, 4H), 4.11–4.13 (m, 2H), 4.55 (d, J=11.5, 2H), 4.71 (d, J=11.5, 2H), 6.93–7.00 (m, 4H), 7.15–7.27 (m, 14H).

Step C. 1,6-di-O-(3-phenyl-1-propyl)-2-O-(4-fluorobenzyl)-D-manntol

The monoalkylated product obtained in step A of this example was treated with p-toluenesulfonic acid in MeOH at room temperature for 18 h. Evaporation of the volatiles in vacuo afforded a residue that was purified by flash chromatography, eluting with 30% EtOAc in hexane, yielding the title compound (73%).

NMR (CDCl$_3$): 1.90 (q, J=6.0, 4H), 2.66 (m, 4H), 3.05 (d, J=5.5, 1H), 3.30 (s, 1H), 3.48–3.54 (m, 4H), 3.55–3.61 (m, 1H), 3.62–3.68 (m, 3H), 3.74 (m, 2H), 3.85 (s, 1H), 3.99 (s, 1H), 4.61 (d, J=11.5, 1H), 4.69 (d, J=11.5, 1H), 7.00 (d, J=8.0, 2H), 7.16–7.19 (m, 6H), 7.25–7.31 (m, 6H).

Example 86
Preparation of 1,6-di-O-(3-phenyl-1-propyl)-2,5-di-O-4-fluorobenzyl-D-mannitol (compound no. 95)

1,6-Di-O-(3-phenyl-1-propyl)-3,4-O-isopropylidene-D-mannitol prepared in step A of example 83 was reacted as in step C of example 83 using p-toluenesulfonic acid in methanol to achieve the removal of the ketal. Purification by flash chromatography eluting with 30% EtOAc in hexane provided 57% of the title compound.

NMR (CDCl$_3$): 1.90 (s, 4H), 2.67 (s, 4H), 3.13 (s, 2H), 3.46–3.47 (m, 4H), 3.68 (s, 2H), 3.68–3.72 (m, 4H), 3.92 (s, 2H), 4.58 (d, J=11.0, 2H), 4.70 (d, J=11.0, 2H), 6.99–7.01 (m, 4H), 7.16–7.17 (m, 6H), 7.25–7.29 (m, 8H).

Example 87
Preparation of 1,6-di-O-benzyl-2-O-(4-fluorobenzyl)-5-O-(2-thienylmethyl)-D-mannitol (compound no. 96)

Step A. 1,6-di-O-benzyl-2-O-(4-fluorobenzyl)-3,4-O-isopropylidene-D-mannitol

To a solution of 1,6-di-O-benzyl-3,4-O-isopropylidene-D-mannitol (402 mg, 1 mmol), obtained as in example 2, in toluene (10 mL) was added silver oxide (348 mg, 1.5 mmol) and 4-fluorobenzyl bromide (375 mg, 1.2 mmol). The mixture was stirred at room temperature for 15 h. The insoluble material was filtered off and the filtrate was evaporated to dryness affording crude 1,6-di-O-benzyl-2-O-(4-fluorobenzyl)-3,4-O-isopropylidene-D-mannitol. The compound was purified by flash chromatography using 30% EtOAc in hexane to yield 93% of desired product.

Step B. 1,6-di-O-benzyl-2-O-(4-fluorobenzyl)-5-O-(2-thienylmethyl)-D-mannitol

Sodium hydride (9.6 mg, 0.4 mmol) was added in portions to a solution of 1,6-di-O-benzyl-2-O-(4-fluorobenzyl)-5-O-(2-thienylmethyl)-D-mannitol (100 mg, 0.20 mmol) in DMF (3 mL). After stirring for a period of 10 minutes, 2-thienylmethyl chloride (264 mg, 0.2 mmol) in DMF (1 mL) was added dropwise and the reaction mixture was stirred at room temperature for 3 h. 1N HCl was then added and the resulting mixture was extracted twice with EtOAc. The organic layer was dried over magnesium sulfate and concentrated in vacuo. The residue was taken up in 5% HCl in MEOH and the reaction was stirred at room temperature for 5 h. Water was added and the reaction mixture was extracted with EtOAc. The organic layer was dried over magnesium sulfate and concentrated in vacuo. The resulting residue was purified by flash chromatography using 30% EtOAc in hexane to provide the title compound in 72% yield.

NMR (CDCl$_3$): 2.90 (d, J=5.5, 1H), 2.96 (d, J=5.5, 1H), 3.65 (dd, J=10.5, 5.5, 2H), 3.75 (m, 4H), 3.90 (m, 2H), 4.55 (d, J=11.0, 1H), 4.61 (s, 4H), 4.68 (d, J=11.0, 1H), 4.77 (d, J=13.0, 1H), 4.91 (d, J=12.5, 1H), 6.97 (m, 3H), 7.03 (t, J=9.0, 2H), 7.10 (t, J=7.5, 2H), 7.27 (m, 5H), 7.39 (t, J=7.5, 2H).

Example 88
Preparation of 1,6-di-O-(2-fluorobenzyl)-2-O-(4-fluorobenzyl)-5-O-(2-thienylmethyl)-D-mannitol (compound no. 97)

Following the indications of step A of example 70, but using 1,6-di-O-(2-fluorobenzyl)-3,4-O-isopropylidene-D-mannitol, the monoalkylation with 4-fluorobenzyl bromide afforded an intermediate that was then alkylated with 2-thienylnethyl chloride. Purification by flash chromatography with 30% EtOAc in hexane afforded the title compound in 75% yield.

NMR (CDCl$_3$): 2.90 (d, J=5.5, 1H), 2.97 (d, J=7.5, 1H), 3.67 (dd, J=10.5, 5.0, 2H), 3.78 (m, 4H), 3.88 (t, J=6.2, 1H), 3.92 (t, J=6.3, 1H), 4.54 (d, J=11.0, 1H), 4.61 (s, 4H), 4.69 (d, J=11.8, 1H), 4.78 (d, J=11.6, 1H), 4.94 (d, J=12.5, 1H), 6.90–7.40 (m, 15H).

Example 89
Preparation of 1,6-di-O-benzyl-2,5-di-O-benzoyl-D-mannitol (compound no. 109)

To a stirred solution of 1,6-di-O-benzyl-3,4-isopropylidene-D-mannitol (50 mg, 0.12 mmol), as obtained in example 2, in methylenechloride (2 mL) and pyridine (2 mL) was added dropwise benzoyl chloride (50 mg, 0.36 mmol) at 0° C. The reaction mixture was stirred for 1 h at 0° C. and 3 h at room temperature. The mixture was poured onto cold 6N HCl (5 mL) and extracted with EtOAc. The organic layer was dried with magnesium sulfate and concentrated in vacuo. The resulting crude material was dissolved in MeOH containing 5% concentrated HCl (3 mL). After 5 h, saturated sodium bicarbonate was added and the mixture was extracted with EtOAc. The organic layer was dried over magnesium sulfate, concentrated in vacuo, and the residue was purified by flash chromatography eluting with 50% EtOAc in hexane to yield 85% of the title compound.

NMR (CDCl$_3$): 3.28 (d, J=6.1, 1H), 3.90 (m, 2H), 4.02 (t, J=7.5, 1H), 4.51 (d, J=12.4, 1H), 4.57 (d, J=11.2, 1H), 7.03 (s, 5H), 7.43 (t, J=7.3, 2H), 7.57 (t, J=7.3, 1H), 8.04 (d, J=7.6, 2H).

Example 90
Preparation of 1,6-di-O-benzoyl-2,5-di-O-benzyl-D-mannitol (compound no. 110)

Following the indications found in example 89, 2,5-di-O-benzyl-3,4-O-isopropylidene-D-mannitol was benzoylated in a 90% yield.

NMR (CDCl$_3$): 2.83 (d, J=7.5, 1H), 3.89 (m, 1H), 4.07 (t, J=7.5, 1H), 4.53 (dd, J=11.5, 4.5, 1H), 4.56 (d, J=11.5, 1H), 4.72 (dd, J=11.5, 7.5, 1H), 4.77 (d, J=11.0, 1H), 7.25 (m, 5H), 7.40 (t, J=8.0, 2H), 7.55 (t, J=7.5, 1H), 8.02 (d, J=8.0, 2H).

Example 91
Preparation of 1,6-di-O-benzyl-2,5-di-O-(methylthiothioxo)-D-mannitol (compound no. 101)

To a solution of 1,6-dibenzyl-3,4-isopropylidene-D-mannitol (40 mg, 0.1 mmol), obtained as in example 2, in DMF (3 mL) was added sodium hydride (7.2 mg, 0.3 mmol). After stirring for 20 min, carbon disulfide was added and stirring was continued for 30 min. Methyl iodide (42 mg, 0.3 mmol) was added and the mixture was stirred for another 15 min. The reaction mixture was quenched with 1N HCl and the organic material was extracted with EtOAc. The organic layer was dried over magnesium sulfate and concentrated in vacuo. The residue was dissolved in MeOH containing 3% HCl (3 mL) and the mixture was stirred for 3 h. Water was added and the mixture was extracted with EtOAc. The organic layer was dried over magnesium sulfate and concentrated in vacuo. The title compound was obtained in 79% yield after purification by flash chromatography eluting with 20% EtOAc in hexane.

NMR (CDCl$_3$): 2.57 (s, 3H), 3.03 (d, J=6.0, 1H), 3.87 (dd, J=11.5, 4.5, 1H), 3.94 (dd, J=11.0, 3.5, 1H), 4.05 (t, J=7.5, 1H), 4.53 (d, J=11.0, 1H), 4.59 (d, J=11.0, 1H), 5.88 (m, 1H), 7.30 (m, 5H).

Example 92
Preparation of 1,6-di-O-benzyl-2,5-di-O-(benzylthiothioxo)-D-mannitol (compound no. 102)

Following the indications of example 91 but substituting methyl iodide with benzyl bromide, the title compound was obtained in 73% yield.

NMR (CDCl3): 3.03 (d, J=5.5, 1H), 3.85 (dd, J=5.5, 11.0, 1H), 3.91 (dd, J=12.0, 5.5, 1H), 4.02 (t, J=7.5, 1H), 4.34 (s, 2H), 4.50 (d, J=11.5, 1H), 4.57 (J=11.5, 1H), 5.87 (m, 1H), 7.28 (m, 10H).

Example 93
Preparation of 1,6-di-O-(2-fluorobenzyl)-2-O-(4-fluorobenzyl)-5-O-(methylthiothioxo)-D-mannitol (compound no. 103)

Using a procedure similar to the above example 91, substituting 1,6-di-O-benzyl-3,4-O-isopropylidene-D-mannitol by 1,6-di-O-(2-fluorobenzyl)-2-O-(4-fluorobenzyl)-3,4-O-isopropylidene-D-mannitol, the title compound was obtained in 79% yield.

NMR (CDCl$_3$): 2.55 (s, 3H), 2.88 (d, J=7.0, 1H), 2.99 (d, J=4.5, 1H), 3.70 (m, 2H), 3.79 (d, J=9.5, 1H), 3.95 (m, 2H), 4.23 (t, J=7.5, 1H), 4.63 (m, 6H), 5.87 (m, 1H), 6.97 (m, 2H), 7.03 (m, 2H), 7.10 (t, J=7.0, 2H), 7.28 (m, 4H), 7.38 (m, 2H).

Example 94
Preparation of 1,2,6-tri-O-benzyl-5-O-(methylthiothioxo)-D-mannitol (compound no. 104)

Using a procedure similar to the above example 91, substituting 1,6-di-O-benzyl-3,4-O-isopropylidene-D-mannitol by 1,2,6-tri-O-benzyl-3,4-O-isopropylidene-D-mannitol, obtained as in example the title compound was obtained in 71% yield.

NMR (CDCl$_3$): 2.53 (s, 3H), 2.90 (d, J=5.0, 2H), 3.70 (m, 2H), 3.77 (m, 1H), 3.91 (m, 2H), 4.00 (t, J=6.0, 1H), 4.53 (m, 3H), 4.56 (d, J=11.5, 1H), 4.73 (m, 3H), 5.00 (d, J=12.5, 1H), 7.30 (m, 15H).

Example 95
Preparation of 1,2,6-tri-O-benzyl-5-O-(allylthiothioxo)-D-mannitol (compound no. 105)

Using a procedure similar to tile above example 91, substituting 1,6-di-Obenzyl-3,4-O-isopropylidene-D-mannitol by 1,2,6-tri-O-benzyi-3,4-O-sopropyiidene-D-mannitol, obtained as in example the title compound was obtained in 81% yield.

NMR (CDCl$_3$): 2.87 (d, J=7.0, 1H), 3.67 (m, 2H), 3.77 (m, 3H), 3.90 (m, 2H), 4.00 (t, J=6.5, 1H), 4.56 (m, 4H), 4.71 (m, 4H), 5.00 (d, J=11.5, 1H), 5.15 (d, J=10.0, 1H), 5.27 (d, J=15.5, 1H), 5.87 (m, 1H), 7.30 (m, 15H).

Example 96
Preparation of 1,6-di-O-benzyl-2-O-(4-fluorobenzyl)-5-O-(methylthiothioxo)-D-mannitol (compound no. 106)

Using a procedure similar to the above example 91, substituting 1,6-di-O-benzyl-3,4-O-isopropylidene-D-mannitol, obtained as in example 70, by 1,6-tri-O-benzyl-2-O-(4-fluorobenzyl)-3,4-O-isopropylidene-D-mannitol, the title compound was obtained in 71% yield.

NMR (CDCl$_3$): 2.55 (s, 3H), 2.89 (d, J=7.0, 1H), 2.99 (d, J=4.5, 1H), 3.72 (m, 3H), 3.77 (d, J=9.5, 1H), 3.95 (m, 2H), 4.23 (t, J=7.5, 1H), 4.63 (m, 6H), 5.87 (m, 1H), 6.98 (m, 2H), 7.03 (m, 2H), 7.11 (t, J=8.0, 2H), 7.27 (m 4H), 7.38 (m, 2H).

Example 97
Preparation of 1,2,6-tri-O-benzyl-5-O-(methyloxycarbonyl)-D-mannitol (compound no. 107)

Using a procedure similar to the above example 91, 1,2,6-tri-O-benzyl-3,4-O-isopropylidene-D-mannitol, obtained as in example 71 was reacted with methyichloroformate to yield 22% of the title compound.

NMR (CDCl$_3$): 2.82 (d, J=5.5, 1H), 2.95 (d, J=5.5, 1H), 3.60–3.80 (m, 8H), 3.99 (t, J=6.6, 1H), 4.30 (q, J=7.4.7, 11.7, 1H), 4.54 (s, 3H), 4.57 (d, J=9.7, 1H), 4.71 (d, J=9.2, 1H), 4.73 (d, J=9.3, 1H), (s, 15H).

Example 98
Preparation of 1,6-di-O-phenyl-2,5-di-O-benzyl-D-mannitol

Step A. 3,4-O-isopropylidene-D-mannitol-1,2-5,6-diepoxide

The title diepoxide was prepared from 3,4-O-isopropylidene-D-mannitol according to the indications found in Heterocycles vol. 25, p. 541–548 (1987).

Step B. 1,6-di-O-phenyl-3,4-O-isopropylidene-D-mannitol

To the diepoxide prepared as in step A of this example (500 mg, 2.70 mmol) and phenol (10 g, 11.0 mmol) in DMF (10 mL) was added potassium carbonate (180 mg, 1.30 mmol). The reaction mixture was heated at 110° C. for 7 h and then cooled to room temperature. A saturated solution of sodium bicarbonate (20 mL) was then added. The mixture was extracted with ether, the organic layer was washed with water, dried over magnesium sulfate and concentrated to give an oil that eventually solidified after maintaining it under high vacuum. Purification by flash chromatography using 30% EtOAc in hexane afforded the title compound in 51% yield, mp. 117° C.

NMR (CDCl$_3$): 1.38 (s, 3H), 3.81 (s, 1H), 4.00–4.04 (m, 3H), 4.23 (d, J=8.3, 1H), 6.94 (d,J=8.2, 2H), 6.96 (t, J=7.2, 2H), 7.27 (t, J=8.0, 2H).

Step C. 1,6-di-O-phenyl-2,5-di-O-benzyl-D-mannitol

The product obtained in step A of this example was alkylated with benzyl bromide as indicated in example 3. Purification by flash chromatography eluting with 20% EtOAc provided the title compound (mp. 80° C.) in a 90% yield.

NMR (CDCl$_3$): 2.90 (d, J=5.9, 1H), 3.98 (m, 1H), 4.08 (t, J=6.3, 1H), 4.13) dd, J=7.3, 13.5, 1H), 4.27 (dd, J=1.9, 12.3, 1H), 4.63 (d, J=11.2, 1H), 4.81 (d, J=11.8, 1H), 6.95 (m, 4H), 7.30 (m, 10H).

Example 99
Preparation of 1,6-deoxy-1,6-dibenzylthio-2,5-O-di-(4-fluorobenzyl)-D-mannitol Step A. 1,6-dideoxy-1,6-dibenzylthio-2,5-di-O-(4-fluorobenzyl)-3,4-O-isopropylidene-D-mannitol To a cooled solution (−5° C.) of diethylazidocarboxylate (4.5 mg, 0.26 mmol) in THF (1 mL) was added 2,5-di-O-(4-fluorobenzyl)-3,4-O-isopropylidene-D-mannitol (38 mg, 0.086 mmol), obtained as in example in THF (2 mL) and triphenylphosphine (6.8 mg, 0.26 mmol).

After 15 min, benzylthiol (32 mg, 3.0 mmol) was added and the reaction mixture was allowed to warm to room temperature. It was stirred overnight, the solvent was removed in vacuo and the crude material was purified by flash chromatography eluting with 20% EtOAc in hexane to yield the desired 1,6-dideoxy-1,6-dibenzylthio-2,5-di-O-(4-fluorobenzyl)-3,4-O-isopropylidene-D-mannitol (32%). The resulting isopropylidene derivative was removed by treatment with methanolic Hcl to provide a 91% yield of the title compound.

NMR (CDCl$_3$): 2.65–2.75 (m, 2H), 2.78 (s, 1H), 3.67 (s, 1H), 3.72 (s, 2H), 3.90 (s, 1H), 4.43 (d, J=11.0, 1H), 4.60 (d, J=11.0, 1H), 6.90–7.02 (m, 2H), 7.22–7.33 (m, 7H).

Example 100
Preparation of 1,6-di-S-benzoyl-2,5-O-di-O-(4-fluorobenzyl)-D-mannitol Substituting benzylthiol by thiobenzoic acid under the condition described in the previous example, the title compound was obtained in 76% yield.

NMR (CDCl$_3$): 3.12 (d, J=5.5, 1H), 3.46 (dd, J=11.0, 5.5, 1H), 3.54 (dd, J=11.0, 5.5, 2H), 3.89 (m, 2H), 4.55 (d, J=11.5, 1H), 4.72 (d, J=10.5, 1H), 7.21 (t, J=3.5, 3H),), 7.27 (t, J=3.5, 2H), 7.45 (J=7.5, 2H), 7.58 (t, J=7.0, 1H), 7.97 (d, J=8.5, 2H).

Example 101
Preparation of 1-O-benzyl-6-O-(2-fluorobenzyl)-2,5-di-O-(4-fluorobenzyl)-D-mannitol (compound no. 63)

Step A. 1-O-benzyl-6-O-(2-fluorobenzyl)-3,4-O-isopropylidene-D-mannitol

1-O-(2-fluorobenzyl)-3,4-isopropylidene-D-mannitol was prepared using the conditions found in example 2, except that 1.5 equivalent of 2-fluorobenzyl bromide was used. Purification by flash chromatography afforded 68% of the monoalkylated product. The resulting product was then alkylated as in example 2 using benzyl bromide. After purification by flash chromatography, eluting with 50% EtOAc in hexane, 82% of the title compound was obtained.

NMR (CDCl$_3$): 1.34 (s, 6H), 3.54–3.62 (m, 4H), 3.72–3.82 (m, 4H), 4.57 (d, J=3.5, 2H), 4.65 (d, J=4.5, 2H), 7.00 (t, J=9.0, 1H), 7.11 (J=7.5, 1H), 7.22–7.30 (m, 2H), 7.32–7.35 (m, 4H), 7.42 (t, J=7.5, 1H).

Step B. 1-O-benzyl-6-O-(2-fluorobenzyl)-2,5-di-O-(4-fluorobenzyl)-D-mannitol

The alkylation of the product of step A of this example was alkylated with benzyl bromide as in example 4 with a yield of 78%.

NMR (CDCl$_3$): 2.48–3.02 (m, 2H), 3.65–3.89 (m, 6H), 3.90–3.95 (m, 2H), 4.53 (s, 4H), 4.56 (d, J=11.5, 1H), 4.60 (d, J=11.5, 1H), 4.66 (d, J=11.0, 1H), 4.69 (d, J=11.0, 1H), 6.90–7.15 (m, 6H), 7.25–7.42 (m, 11H).

Example 102
Preparation of 1,6-di-O-(2-fluorobenzyl)-2-O-benzyl-5-O-(4-fluorobenzyl)-D-mannitol (compound no. 62)

The alkylation of 3,4-O-isopropylidene-D-mannitol was performed according to the indications found in example 2. The 1,6-di-O-(2-fluorobenzyl)-3,4-O-isopropylidene-D-mannitol was then alkylated with benzyl bromide using the silver oxide conditions with 1.5 equivalent of benzyl bromide as in step A of example 70. The resulting 1,6-di-O-(2-fluorobenzyl)-2-O-benzyl-3,4-O-isopropylidene-D-mannitol was then alkylated with 4-fluorobenzyl bromide as in example 4, leading to 82% of the title product.

NMR (CDCl$_3$): 2.98 (d, J=5.5, 1H), 3.00 (d, J=7.5, 1H), 3.67–3.71 (m, 2H), 3.70–3.79 (m, 4H), 3.90–3.95 (m, 2H), 4.53 (d, J=11.5, 1H), 4.58 (d, J=11.5, 1H), 4.60 (s, 4H), 4.67 (d, J=11.5, 1H), 4.73 (d, J=11.5, 1H), 6.95–7.11 (m, 6H), 7.24–7.40 (m, 11H).

Example 103
Preparation of 1,2,6-tri-O-benzyl-5-O-(4-nitrobenzyl)-D-mannitol (compound no. 74)

The product of example 71 was further alkylated with 4-nitrobenzyl bromide affording after purification by flash chromatography the title compound.

NMR (CDCl$_3$): 2.43 (d, J=2.5, 1H), 2.67 (d, J=5.51H), 3.62–3.69 (m, 2H) 2.75 (d, J=12.5, 2H), 3.79 (d, J=12.5, 2H), 3.78 (dd, J=9.0, 5.5, 1H), 4.07 (d, J=6.0, 1H), 4.52 (s, 2H), 4.56 (s, 2H), 4.68j (s, 2H), 4.68 (d, J=12.8, 1H), 4.90 (d, J=12.8, 1H), 7.25–7.35 (m, 15H), 7.44 (d, J=9.2H), 8.10 (d, J=7.5, 2H).

Example 104
1,2,5,6-tetra-O-benzyl-D-mannitol—Results on HIV-infected Cells

The Ki of protease inhibition was found to be 0.28 µM and the cytotoxicity was found to be 15 µM. The assay against HIV infected cells was 4.8 µM.

Technical Details (antiviral tests)

Cells were acutely infected with HIV-1 at a M.O.I. (multiplicity of infection) of 0.01 at 37° C. for 2 hours. After adsorption, the cells were washed to remove unadsorbed virus and plated in 96-well or 24-well microplates in culture medium containing the protease inhibitors at various concentrations. The infected cells were grown for 7 or 10 days at 37° C. with the culture medium replaced every 3 to 4 days with fresh medium containing inhibitors. Aliquots from the cell culture supernatants were collected and frozen at −70° C. for subsequent viral titer determination.

Reverse transcriptase activity was measured by standard procedures. The samples were centrifuged at 4° C. for 45 min at 45000 RPM and the virus pellets resuspended in 500 µL of buffer (Tris-HCl 10 mM, pH 7.8, NaCl 100 mM, EDTA 1 mM) containing 0.1% Triton X-100. For the assay, 20 µL of suspension was added to 40 µL of reaction buffer (Tris-HCl 60 mM, pH 8.0, MgCl$_2$ 6 mM, KCl 25 mM, DTT 1 mM, 125 ng poly(rA) and oligo(dT)12–18, and 5 µCi of $^3$H-TTP). The reaction was done at 37° C. for 1 h after which the incorporated radioactivity was precipitated with TCA. After filtration, the radioactivity incorporated by the viral reverse transcriptase in the template was measured with a scintillation counter.

P24 determination was done in cell-free supernatants using the p24 antigen-capture assay of Coulter Immunology or SAIC Frederick, according to the manufacturer's recommendations.

Inhibition of syncytia formation was assessed by periodic microscope examination under low, magnification of infected cells incubated with the protease inhibitors at different concentrations.

Example 105
1,2,5,6-tetra-O-benzyl-D-mannitol—Toxicity on Cells

The Ki of protease inhibition was found to be 0.28 µM and the cytotoxicity was found to be 15 µM. The assay against HIV infected cells was 4.8 µM.

Technical Details:

Two assays were performed to evaluate the potentiel toxicity of the compounds in infected cells:

1) Briefly, cells were grown in 96-well microtiter plates at 37° C. in complete culture medium in the presence of the compound to test. Control cells grown in the absence of the compound received the same amount of solvent used to dissolve the inhibitor (in this case, dimethylsulfoxide at a final concentration of 0.1 to 0.3%). After 7 or 10 days, MTT was added to the cultures for 4 hours at 37° C. as described in the literature (Schwartz et al., AIDS Res. Hum. Retrov. 4: 441–448, 1988; Mosmaun, J. Immunol. Meth., 65: 55–63, 1983) and the changes in absorbance associated with metabolism of MTT by viable cells was monitored with an ELISA microplate reader at a test wavelength of 540 nm.

2) The cells were grown as described above in 24-well microplates or 25-cm tissue culture flasks in the presence or absence of the tested compounds, and the cell viability after 7 or 10 days was determined by the trypan blue exclusion test, using a hemacytometer and a microscope at 100× magnification.

We claim:

1. A mannitol derivative selected from the group consisting of a compound of formula 1:

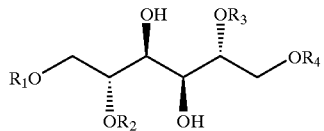

and when a compound of formula 1 comprises a carboxylic acid group pharmaceutically acceptable salts thereof and when a compound of formula 1 comprises an amino group pharmaceutically acceptable ammonium salts thereof, wherein $R_1$ and $R_4$ are the same, wherein $R_2$ and $R_3$ are the same, wherein $R_1$ and $R_4$ are the same as or different from $R_2$ and $R_3$, wherein, when $R_1$ and $R_4$ are the same as $R_2$ and $R_3$, $R_1$, $R_2$, $R_3$ and $R_4$ are selected from the group consisting of substituted benzyl, wherein, when $R_1$ and $R_4$ are different from $R_2$ and $R_3$, $R_1$, $R_2$, $R_3$ and $R_4$ are selected from the group consisting of unsubstituted benzyl and substituted benzyl, substituted benzyl being benzyl which is substituted by one or more members of the group consisting of —Cl, —F, —Br, —I, —CN, —A—CN, —CF$_3$, —A—CF$_3$, —NO$_2$, R$_5$—CO, R$_5$—CO—A—, —OCH$_2$C$_6$H$_5$, —A—S(O)$_n$—R$_5$, straight or branched C$_1$ to C$_6$ alkyl, —A—OR$_5$, —OR'$_5$, —NR$_6$R$_7$, —A—NR$_6$R$_7$, —COOR$_8$, —A—COOR$_8$, —A—NHCOR$_8$, —NHCOOR$_8$ and —A—NHCOOR$_8$, wherein n denotes 0, 1 or 2, and wherein A represents an alkylene group having from 1 to 5 carbon atoms, $R_5$ is selected from the group consisting of H, straight or branched $C_1$ to $C_6$ alkyl, straight or branched $C_2$ to $C_6$ alkenyl, $C_4$ to $C_{11}$ methylcycloalkyl, unsubstituted phenyl, phenyl which is substituted by one or more members of the group consisting of —Cl, —F, —Br, —I, —CN, —A—CN, —CF$_3$, —A—CF$_3$, —NO$_2$, —OCH$_2$C$_6$H$_5$, and straight or branched $C_1$ to $C_6$ alkyl, —A— being as defined above, benzimidazolyl, imidazolyl, imidazolinyl, imidazolidinyl, quinolyl, isoquinolyl, indolyl, pyridyl, pyrrolyl, pyrrolinyl, pyrrolidinyl, pyrazolyl, pyrazinyl, quinoxolyl, piperidinyl, morpholinyl, β-carbolinyl, tetrazolyl, thiazolidinyl, benzofuranyl, thiamorpholinyl, benzoxazolyl, oxopiperidinyl, oxopyrrolidinyl, oxoazepinyl, azepinyl, isoxazolyl, tetrahydropyranyl, tetrahydrofuranyl, thiadiazolyl, thiadiazinyl, benzodioxolyl, thiophenyl, tetrahydrothiophenyl, nicoticoyl, morpholinecarbodithioyl and sulfolanyl, $R'_5$ is selected from the group consisting of H, straight or branched $C_2$ to $C_6$ alkenyl, $C_4$ to $C_{11}$ methylcycloalkyl, unsubstituted phenyl, phenyl which is substituted by one or more members of the group consisting of —Cl, —F, —Br, —I, —CN, —A—CN, —CF$_3$, —A—CF, —NO$_2$, —OCH$_2$C$_6$H$_5$, and straight or branched $C_1$ to $C_6$ alkyl, —A— being as defined above, benzimidazolyl, imidazolyl, imidazolinyl, imidazolidinyl, quinolyl, isoquinolyl, indolyl, pyridyl, pyrrolyl, pyrrolinyl, pyrrolidinyl, pyrazolyl, pyrazinyl, quinoxolyl, piperidinyl, morpholinyl, β-carbolinyl, tetrazolyl, thiazolidinyl, benzofuranyl, thiamorpholinyl, benzoxazolyl, oxopiperidinyl, oxopyrrolidinyl, oxoazepinyl, azepinyl, isoxazolyl, tetrahydropyranyl, tetrahydrofuranyl, thiadiazolyl, thiadiazinyl, benzodioxolyl, thiophenyl, tetrahydrothiophenyl, nicoticoyl, morpholinecarbodithioyl and sulfolanyl, $R_6$ and $R_7$ are each independently selected from the group consisting of H, straight or branched $C_1$ to $C_6$ alkyl, straight or branched $C_2$ to $C_6$ alkenyl, $C_4$ to $C_{11}$ methylcycloalkyl, unsubstituted phenyl, phenyl which is substituted by one or more members of the group consisting of —Cl, —F, —Br, —I, —CN, —A—CN, —CF$_3$, —A—CF$_3$, —NO$_2$, —OCH$_2$C$_6$H$_5$, and straight or branched $C_1$ to $C_6$ alkyl, —A— being as defined above, benzimidazolyl, imidazolyl, imidazolinyl, imidazolidinyl, quinolyl, isoquinolyl, indolyl, pyridyl, pyrrolyl, pyrrolinyl, pyrrolidinyl, pyrazolyl, pyrazinyl, quinoxolyl, piperidinyl, morpholinyl, β-carbolinyl, tetrazolyl, thiazolidinyl, benzofuranyl, thiamorpholinyl, benzoxazolyl, oxopiperidinyl, oxopyrrolidinyl, oxoazepinyl, azepinyl, isoxazolyl, tetrahydropyranyl, tetrahydrofuranyl, thiadiazolyl, thiadiazinyl, benzodioxolyl, thiophenyl, tetrahydrothiophenyl, nicoticoyl, morpholinecarbodithioyl and sulfolanyl or $R_6$ and $R_7$ together with the nitrogen atom to which they are bonded represent a saturated or unsaturated heterocyclic group of formula

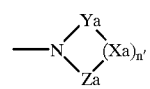

wherein Ya and Za each independently denotes a normal hydrocarbon chain comprising 1 to 3 carbon atoms, Xa denotes O and n' denotes 0 or 1, provided that when n' denotes 1 Ya and Za cannot both comprise 3 carbon atoms at the same time and that when n' denotes 0 Ya and Za are bonded directly together, and $R_8$ is selected from the group consisting of H, straight or branched $C_1$ to $C_6$ alkyl, straight or branched $C_2$ to $C_6$ alkenyl, $C_4$ to $C_{11}$ methylcycloalkyl, unsubstituted phenyl, phenyl which is substituted by one or more members of the group consisting of —Cl, —F, —Br, —I, —CN, —A—CN, —CF$_3$, —A—CF$_3$, —NO$_2$, —OCH$_2$C$_6$H$_5$, and straight or branched $C_1$ to $C_6$ alkyl, —A— being as defined above, benzimidazolyl, imidazolyl, imidazolinyl, imidazolidinyl, quinolyl, isoquinolyl, indolyl, pyridyl, pyrrolyl, pyrrolinyl, pyrrolidinyl, pyrazolyl, pyrazinyl, quinoxolyl, piperidinyl, morpholinyl, β-carbolinyl, tetrazolyl, thiazolidinyl, benzofuranyl, thiamorpholinyl, benzoxazolyl, oxopiperidinyl, oxopyrrolidinyl, oxoazepinyl, azepinyl, isoxazolyl, tetrahydropyranyl, tetrahydrofuranyl, thiadiazolyl, thiadiazinyl, benzodioxolyl, thiophenyl, tetrahydrothiophenyl, nicoticoyl, morpholinecarbodithioyl and sulfolanyl.

2. A mannitol derivative as defined in claim 1 herein $R_1$ and $R_4$ are the same and each denote an unsubstituted benzyl, where $R_2$ and $R_3$ are the same and each denote a benzyl group of formula

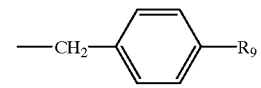

wherein $R_9$ is selected from the group consisting of —Cl, —F, —Br, —CN, —CF$_3$, —NO$_2$, —CHO, —OCH$_2$C$_6$H$_5$, —CH$_3$, —NH$_2$, —OH, —COOCH$_3$, —COOH, —CH$_2$NH$_2$, —CONH$_2$, —NH— tert-butyloxycarbonyl and —NHCOOR$_{10}$ wherein $R_{10}$ is —H or tert-butyl.

3. A mannitol derivative as defined in claim 1 wherein $R_2$ and $R_3$ are the same and each denote an unsubstituted benzyl, where $R_1$ and $R_4$ are the same and each denote a benzyl group of formula

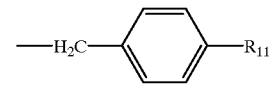

wherein $R_{11}$ is selected from the group consisting of —Cl, —F, —Br, —CN, —CF$_3$, —NO$_2$, —CH$_2$OH, —CH$_3$, —NH$_2$, —COOR$_{12}$, —COOH wherein $R_{12}$ is methyl or iso-butyl.

4. A mannitol derivative of formula 1 as defined in claim 1 wherein $R_1$ and $R_4$ are the same and each denote a benzyl group of formula

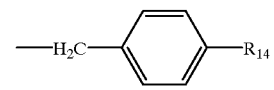

wherein $R_{14}$ is selected from the group consisting of —F, —CN, CF$_3$, —OH, —CH$_3$ and OCH$_2$C$_6$H$_5$ and wherein $R_2$ and $R_3$ are the same and each denote a benzyl group of formula

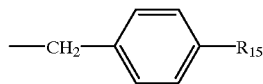

wherein $R_{15}$ is selected from the group consisting of —F, —CN, —$CF_3$, —OH and $CH_3$.

5. A mannitol derivative of formula 1 as defined in claim 1 wherein $R_1$ denotes a substituted benzyl group of formula

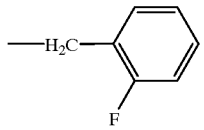

and wherein $R_2$, $R_3$ and $R_4$ each denote an unsubstituted benzyl group.

6. A mannitol derivative of formula 1 as defined in claim 1 wherein $R_2$ and $R_3$ each denotes a substituted benzyl group of formula

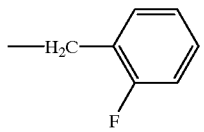

and wherein $R_1$ and $R_4$ each denote an unsubstituted benzyl group.

7. A mannitol derivative of formula 1 as defined in claim 1 wherein $R_1$ and $R_4$ denote a substituted benzyl group of formula

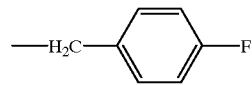

and wherein $R_2$ and $R_3$ each denote an unsubstituted benzyl group.

8. A mannitol derivative of formula 1 as defined in claim 1 wherein $R_2$ and $R_3$ denote a substituted benzyl group of formula

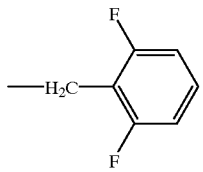

and wherein $R_1$ and $R_4$ each denote a benzyl group of formula

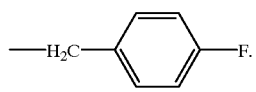

9. A mannitol derivative of formula 1 as defined in claim 1 wherein $R_2$ and $R_3$ denote a benzyl group of formula

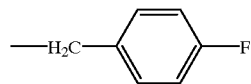

and wherein $R_1$ and $R_4$ each denote a benzyl group of formula

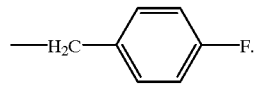

10. A mannitol derivative of formula 1 as defined in claim 1 wherein $R_3$ denotes a benzyl group, $R_2$ denotes a benzyl group of formula

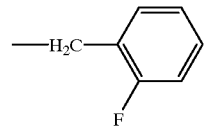

and wherein $R_1$ and $R_4$ each denote a benzyl group of formula

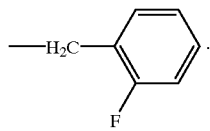

11. A mannitol derivative of formula 1 as defined in claim 1 wherein $R_1$, $R_2$, $R_3$ and $R_4$ are each independently selected from the group consisting of unsubstituted benzyl and benzyl which is substituted by one or more members of the group consisting of F and —OH, and provided that at least one of $R_1$, $R_2$, $R_3$ and $R_4$ is benzyl which is substituted by one or more members of the group consisting of F and —OH.

12. A pharmacuetical composition comprising a pharmacuetically acceptable carrier and a pharmacuetically effective amount of at least one mannitol derivative selected from the group consisting of formula 1:

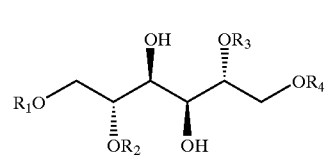

and when a compound of formula 1 comprises a carboxylic acid group pharmaceutically acceptable salts thereof and when a compound of formula 1 comprises an amino group pharmaceutically acceptable ammonium salts thereof, wherein $R_1$ and $R_4$ are the same, wherein $R_2$ and $R_3$ are the same, wherein $R_1$ and $R_4$ are the same as or different from $R_2$ and $R_3$, wherein, when $R_1$ and $R_4$ are the same as $R_2$ and $R_3$, $R_1$, $R_2$, $R_3$ and $R_4$ are selected from the group consisting of substituted benzyl, wherein, when $R_1$ and $R_4$ are different from $R_2$ and $R_3$, $R_1$, $R_2$, $R_3$ and $R_4$ are selected from the group consisting of unsubstituted benzyl and substituted benzyl, substituted benzyl being benzyl which is substituted by one or more members of the group consisting of —Cl, —F, —Br, —I, —CN, —A—CN, —CF$_3$, —A—CF$_3$, —NO$_2$, R$_5$—CO, R$_5$—CO—A—, —OCH$_2$C$_6$H$_5$, —A—S(O)$_n$—R$_5$, straight or branched C$_1$ to C$_6$ alkyl, —A—OR$_5$, —OR'$_5$, —NR$_6$R$_7$, —A—NR$_6$R$_7$, —COOR$_8$, —A—COOR$_8$, —A—NHCOR$_8$, —NHCOOR$_8$ and —A—NHCOOR$_8$, wherein n denotes 0, 1 or 2, and wherein A represents an alkylene group having from 1 to 5 carbon atoms, R$_5$ is selected from the group consisting of H, straight or branched C$_1$ to C$_6$ alkyl, straight or branched C$_2$ to C$_6$ alkenyl, C$_4$ to C$_{11}$ methylcycloalkyl, unsubstituted phenyl, phenyl which is substituted by one or more members of the group consisting of —Cl, —F, —Br, —I, —CN, —A—CN, —CF$_3$, —A—CF$_3$, —NO$_2$, —OCH$_2$C$_6$H$_5$, and straight or branched C$_1$ to C$_6$ alkyl, —A— being as defined above, benzimidazolyl, imidazolyl, imidazolinyl, imidazolidinyl, quinolyl, isoquinolyl, indolyl, pyridyl, pyrrolyl, pyrrolinyl, pyrrolidinyl, pyrazolyl, pyrazinyl, quinoxolyl, piperidinyl, morpholinyl, β-carbolinyl, tetrazolyl, thiazolidinyl, benzofuranyl, thiamorpholinyl, benzoxazolyl, oxopiperidinyl, oxopyrrolidinyl, oxoazepinyl, azepinyl, isoxazolyl, tetrahydropyranyl, tetrahydrofuranyl, thiadiazolyl, thiadiazinyl, benzodioxolyl, thiophenyl, tetrahydrothiophenyl, nicoticoyl, morpholinecarbodithioyl and sulfolanyl, R'$_5$ is selected from the group consisting of H, straight or branched C$_2$ to C$_6$ alkenyl, C$_4$ to C$_{11}$ methylcycloalkyl, unsubstituted phenyl, phenyl which is substituted by one or more members of the group consisting of —Cl, —F, —Br, —I, —CN, —A—CN, —CF$_3$, —A—CF$_3$, —NO$_2$, —OCH$_2$C$_6$H$_5$, and straight or branched C$_1$ to C$_6$ alkyl, —A— being as defined above, benzimidazolyl, imidazolyl, imidazolinyl, imidazolidinyl, quinolyl isoquinolyl, indolyl, pyridyl, pyrrolyl, pyrrolinyl, pyrrolidinyl, pyrazolyl, pyrazinyl, quinoxolyl, piperidinyl, morpholinyl, β-carbolinyl, tetrazolyl, thiazolidinyl, benzofuranyl, thiamorpholinyl, benzoxazolyl, oxopiperidinyl, oxopyrrolidinyl, oxoazepinyl, azepinyl, isoxazolyl, tetrahydropyranyl, tetrahydrofuranyl, thiadiazolyl, thiadiazinyl, benzodioxolyl, thiophenyl, tetrahydrothiophenyl, nicoticoyl, morpholinecarbodithioyl and sulfolanyl, R$_6$ and R$_7$ are each independently selected from the group consisting of H, straight or branched C$_1$ to C$_6$ alkyl, straight or branched C$_2$ to C$_6$ alkenyl, C$_4$ to C$_{11}$ methylcycloalkyl, unsubstituted phenyl, phenyl which is substituted by one or more members of the group consisting of —Cl, —F, —Br, —I, —CN, —A—CN, —CF$_3$, —A—CF$_3$, —NO$_2$, —OCH$_2$C$_6$H$_5$, and straight or branched C$_1$ to C$_6$ alkyl, —A— being as defined above, benzimidazolyl, imidazolyl, imidazolinyl, imidazolidinyl, quinolyl, isoquinolyl, indolyl, pyridyl, pyrrolyl, pyrrolinyl, pyrrolidinyl, pyrazolyl, pyrazinyl, quinoxolyl, piperidinyl, morpholinyl, β-carbolinyl, tetrazolyl, thiazolidinyl, benzofuranyl, thiamorpholinyl, benzoxazolyl, oxopiperidinyl, oxopyrrolidinyl, oxoazepinyl, azepinyl, isoxazolyl, tetrahydropyranyl, tetrahydrofuranyl, thiadiazolyl, thiadiazinyl, benzodioxolyl, thiophenyl, tetrahydrothiophenyl, nicoticoyl, morpholinecarbodithioyl and sulfolanyl or R$_6$ and R$_7$ together with the nitrogen atom to which they are bonded represent a saturated or unsaturated heterocyclic group of formula

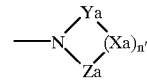

wherein Ya and Za each independently denotes a normal hydrocarbon chain comprising 1 to 3 carbon atoms, Xa denotes O and n' denotes 0 or 1, provided that when n' denotes 1 Ya and Za cannot both comprise 3 carbon atoms at the same time and that when n' denotes 0 Ya and Za are bonded directly together, and R$_8$ is selected from the group consisting of H, straight or branched C$_1$ to C$_6$ alkyl, straight or branched C$_2$ to C$_6$ alkenyl, C$_4$ to C$_{11}$ methylcycloalkyl, unsubstituted phenyl, phenyl which is substituted by one or more members of the group consisting of —Cl, —F, —Br, —I, —CN, —A—CN, —CF$_3$, —A—CF$_3$, —NO$_2$, —OCH$_2$C$_6$H$_5$, and straight or branched C$_1$ to C$_6$ alkyl, —A— being as defined above, benzimidazolyl, imidazolyl, imidazolinyl, imidazolidinyl, quinolyl, isoquinolyl, indolyl, pyridyl, pyrrolyl, pyrrolinyl, pyrrolidinyl, pyrazolyl, pyrazinyl, quinoxolyl, piperidinyl, morpholinyl, β-carbolinyl, tetrazolyl, thiazolidinyl, benzofuranyl, thiamorpholinyl, benzoxazolyl, oxopiperidinyl, oxopyrrolidinyl, oxoazepinyl, azepinyl, isoxazolyl, tetrahydropyranyl, tetrahydrofuranyl, thiadiazolyl, thiadiazinyl, benzodioxolyl, thiophenyl, tetrahydrothiophenyl, nicoticoyl, morpholinecarbodithioyl and sulfolanyl.

13. A pharmaceutical composition as defined in claim 12 wherein R$_1$ and R$_4$ are the same and each denote an unsubstituted benzyl, where R$_2$ and R$_3$ are the same and each denote a benzyl group of formula

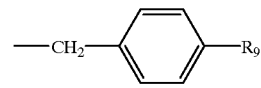

wherein R$_9$ is selected from the group consisting of —Cl, —F, —Br, —CN, —CF$_3$, —NO$_2$, —CHO, —OCH$_2$C$_6$H$_5$, —CH$_3$, —NH$_2$, —OH, —COOCH$_3$, —COOH, —CH$_2$NH$_2$, —CONH$_2$, —NH— tert-butyloxycarbonyl and —NHCOOR$_{10}$ wherein R$_{10}$ is —H or tert-butyl.

14. A pharmaceutical composition as defined in claim 12 wherein R$_2$ and R$_3$ are the same and each denote an unsubstituted benzyl, where R$_1$ and R$_4$ are the same and each denote a benzyl group of formula

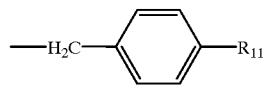

wherein R$_{11}$ is selected from the group consisting of —Cl, —F, —Br, —CN, —CF$_3$, —NO$_2$, —CH$_2$OH, —CH$_3$, —NH$_2$, —COOR$_{12}$, —COOH wherein R$_{12}$ is methyl or iso-butyl.

15. A pharmaceutical composition as defined in claim 12 wherein R$_1$ and R$_4$ are the same and each denote a benzyl group of formula

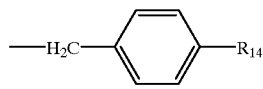

wherein $R_{14}$ is selected from the group consisting of —F, —CN, $CF_3$, —OH, —$CH_3$ and $OCH_2C_6H_5$ and wherein $R_2$ and $R_3$ are the same and each denote a benzyl group of formula

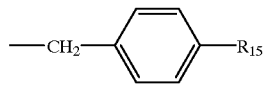

wherein $R_{15}$ is selected from the group consisting of —F, —CN, —$CF_3$, —OH and $CH_3$.

16. A pharmaceutical composition as defined in claim 12 wherein $R_1$ denotes a substituted benzyl group of formula

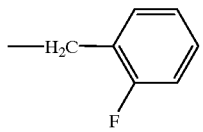

and wherein $R_2$, $R_3$ and $R_4$ each denote an unsubstituted benzyl group.

17. A pharmaceutical composition as defined in claim 12 wherein $R_2$ and $R_3$ each denotes a substituted benzyl group of formula

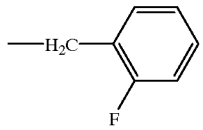

and wherein $R_1$ and $R_4$ each denote an unsubstituted benzyl group.

18. A pharmaceutical composition as defined in claim 12 wherein $R_1$ and $R_4$ denote a substituted benzyl group of formula

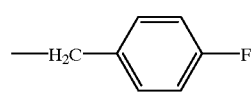

and wherein $R_2$ and $R_3$ each denote an unsubstituted benzyl group.

19. A pharmaceutical composition as defined in claim 12 wherein $R_2$ and $R_3$ denote a substituted benzyl group of formula

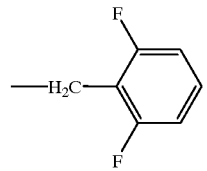

and wherein $R_1$ and $R_4$ each denote a benzyl group of formula

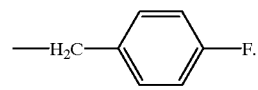

20. A pharmaceutical compostion as defined in claim 12 wherein $R_2$ and $R_3$ denote a substituted benzyl group of formula

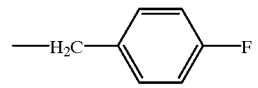

and wherein $R_1$ and $R_4$ each denote a benzyl group of formula

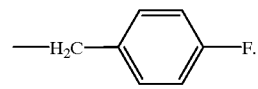

21. A pharmaceutical composition as defined in claim 12 wherein $R_3$ denotes a benzyl group, $R_2$ denotes a benzyl group of formula

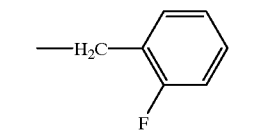

and wherein $R_1$ and $R_4$ each denote a benzyl group of formula

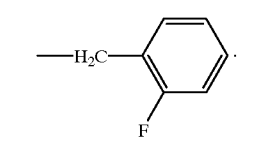

22. A pharmaceutical composition as defined in claim 12 wherein $R_1$, $R_2$, $R_3$ and $R_4$ are each independently selected from the group consisting of unsubstituted benzyl and benzyl which is substituted by one or more members of the group consisting of F and —OH, and provided that at least one of $R_1$, $R_2$, $R_3$ and $R_4$ is benzyl which is substituted by one or more members of the group consisting of F and —OH.

* * * * *